(12) United States Patent
McHugo et al.

(10) Patent No.: US 9,314,356 B2
(45) Date of Patent: Apr. 19, 2016

(54) MECHANICALLY EXPANDABLE DELIVERY AND DILATION SYSTEMS

(75) Inventors: Vincent McHugo, Birdhill (IE); John Neilan, Gort (IE)

(73) Assignee: Cook Medical Technologies LLC, Bloomington, IN (US)

( * ) Notice: Subject to any disclaimer, the term of this patent is extended or adjusted under 35 U.S.C. 154(b) by 910 days.

(21) Appl. No.: 13/015,764

(22) Filed: Jan. 28, 2011

(65) Prior Publication Data

US 2011/0190865 A1    Aug. 4, 2011

Related U.S. Application Data

(60) Provisional application No. 61/299,605, filed on Jan. 29, 2010.

(51) Int. Cl.
*A61F 2/06* (2013.01)
*A61F 2/966* (2013.01)
*A61F 2/95* (2013.01)

(52) U.S. Cl.
CPC . *A61F 2/966* (2013.01); *A61F 2/95* (2013.01); *A61F 2002/9505* (2013.01); *A61F 2002/9511* (2013.01); *A61F 2002/9517* (2013.01); *A61F 2002/9534* (2013.01); *A61F 2002/9665* (2013.01)

(58) Field of Classification Search
CPC ................ A61F 2002/9511; A61F 2002/9522; A61F 2/95; A61F 2002/9534
USPC ....................... 623/1.11, 1.12, 1.23
See application file for complete search history.

(56) References Cited

U.S. PATENT DOCUMENTS

| 1,724,983 | A | 8/1929 | Weiss |
| 3,132,549 | A | 5/1964 | Lee |
| 3,888,258 | A | 6/1975 | Akiyama |
| 3,897,786 | A | 8/1975 | Garnett et al. |

(Continued)

FOREIGN PATENT DOCUMENTS

| CA | 2739275 A1 | 4/2010 |
| EP | 566 807 A1 | 10/1993 |

(Continued)

OTHER PUBLICATIONS

International Search Report completed Mar. 14, 2011 for International Application No. PCT/US2001/022903.

(Continued)

*Primary Examiner* — Katherine Rodjom
(74) *Attorney, Agent, or Firm* — Brinks Gilson & Lione

(57) ABSTRACT

A stent delivery system, a dilator system and a method for implanting a stent are provided. The stent delivery system includes an elongate shaft including a proximal portion, a distal portion, a lumen extending at least partially therethrough, and a stent receiving portion on the distal portion of the shaft. The stent delivery system also includes a stent positioned at the stent receiving portion of the elongate shaft, the stent having a constrained configuration and an expanded configuration. A proximal constraining member and a distal constraining member releasably connected to the stent and having a first position and a second position are also included. The proximal constraining member and the distal constraining member cooperatively apply longitudinal tensile force to at least a portion of the stent with the proximal and distal constraining members each in the first position.

21 Claims, 26 Drawing Sheets

(56) References Cited

U.S. PATENT DOCUMENTS

| | | | |
|---|---|---|---|
| 4,559,041 A | 12/1985 | Razi |
| 4,655,771 A | 4/1987 | Wallsten |
| 4,921,484 A | 5/1990 | Hillstead |
| 5,026,377 A | 6/1991 | Burton et al. |
| 5,275,151 A | 1/1994 | Shockey et al. |
| 5,372,600 A | 12/1994 | Beyar et al. |
| 5,415,664 A | 5/1995 | Pinchuk |
| 5,433,723 A | 7/1995 | Lindenberg et al. |
| 5,443,477 A | 8/1995 | Marin et al. |
| 5,458,615 A | 10/1995 | Klemm et al. |
| 5,554,894 A | 9/1996 | Sepielli |
| 5,681,323 A | 10/1997 | Arick |
| 5,683,451 A | 11/1997 | Lenker et al. |
| 5,690,644 A | 11/1997 | Yurek et al. |
| 5,700,269 A | 12/1997 | Pinchuk et al. |
| 5,702,418 A | 12/1997 | Ravenscroft |
| 5,707,376 A | 1/1998 | Kavteladze et al. |
| 5,709,703 A | 1/1998 | Lukic et al. |
| 5,733,325 A | 3/1998 | Robinson et al. |
| 5,759,186 A | 6/1998 | Bachmann et al. |
| 5,776,142 A | 7/1998 | Gunderson |
| 5,833,694 A | 11/1998 | Poncet |
| 5,906,619 A | 5/1999 | Olson et al. |
| 5,944,727 A | 8/1999 | Ahari et al. |
| 5,968,052 A | 10/1999 | Sullivan, III et al. |
| 5,993,460 A | 11/1999 | Beitelia et al. |
| 6,093,194 A | 7/2000 | Mikus et al. |
| 6,146,415 A | 11/2000 | Fitz |
| 6,162,231 A | 12/2000 | Mikus et al. |
| 6,168,610 B1 | 1/2001 | Marin et al. |
| 6,238,402 B1 | 5/2001 | Sullivan, III et al. |
| 6,254,628 B1 | 7/2001 | Wallace et al. |
| 6,346,118 B1 | 2/2002 | Baker et al. |
| 6,375,676 B1 | 4/2002 | Cox |
| 6,383,211 B1 | 5/2002 | Stachle |
| 6,391,050 B1 | 5/2002 | Broome |
| 6,391,051 B2 | 5/2002 | Sullivan, III et al. |
| 6,402,760 B1 | 6/2002 | Fedida |
| 6,413,269 B1 | 7/2002 | Bui et al. |
| 6,428,566 B1 | 8/2002 | Holt |
| 6,514,261 B1 | 2/2003 | Randall et al. |
| 6,520,983 B1 | 2/2003 | Colgan et al. |
| 6,530,949 B2 | 3/2003 | Konya et al. |
| 6,592,549 B2 | 7/2003 | Gerdts et al. |
| 6,599,296 B1 | 7/2003 | Gillick et al. |
| 6,629,981 B2 | 10/2003 | Bui et al. |
| 6,669,719 B2 | 12/2003 | Wallace et al. |
| 6,673,101 B1 | 1/2004 | Fitzgerald et al. |
| 6,695,862 B2 | 2/2004 | Cox et al. |
| 6,695,875 B2 | 2/2004 | Stelter et al. |
| 6,749,627 B2 | 6/2004 | Thompson et al. |
| 6,755,854 B2 | 6/2004 | Gillick et al. |
| 6,755,855 B2 | 6/2004 | Yurek et al. |
| 6,786,918 B1 | 9/2004 | Krivoruchko et al. |
| 6,808,529 B2 | 10/2004 | Fulkerson |
| 6,821,291 B2 | 11/2004 | Bolea et al. |
| 6,860,898 B2 | 3/2005 | Stack et al. |
| 6,866,669 B2 | 3/2005 | Buzzard et al. |
| 6,890,317 B2 | 5/2005 | Gerdts et al. |
| 6,893,458 B2 | 5/2005 | Cox et al. |
| 6,911,039 B2 | 6/2005 | Shiu et al. |
| 6,926,732 B2 | 8/2005 | Derus et al. |
| 6,939,352 B2 | 9/2005 | Buzzard et al. |
| 6,942,688 B2 | 9/2005 | Bartholf et al. |
| 6,991,646 B2 | 1/2006 | Clerc et al. |
| 7,052,511 B2 | 5/2006 | Weldon et al. |
| 7,122,058 B2 | 10/2006 | Levine et al. |
| 7,335,224 B2 | 2/2008 | Øhlenschlæger |
| 2002/0007206 A1 | 1/2002 | Bui et al. |
| 2002/0095203 A1 | 7/2002 | Thompson et al. |
| 2002/0111666 A1 | 8/2002 | Hart et al. |
| 2002/0183827 A1 | 12/2002 | Derus et al. |
| 2003/0093084 A1 | 5/2003 | Nissan et al. |
| 2003/0144671 A1 | 7/2003 | Brooks et al. |
| 2003/0191516 A1 | 10/2003 | Weldon et al. |
| 2003/0225445 A1 | 12/2003 | Derus et al. |
| 2004/0006380 A1 | 1/2004 | Buck et al. |
| 2004/0010265 A1 | 1/2004 | Karpiel |
| 2004/0093057 A1 | 5/2004 | Bolduc et al. |
| 2004/0181239 A1 | 9/2004 | Dorn et al. |
| 2004/0186547 A1 | 9/2004 | Dorn et al. |
| 2004/0193180 A1 | 9/2004 | Buzzard et al. |
| 2004/0215229 A1 | 10/2004 | Coyle |
| 2004/0220653 A1 | 11/2004 | Borg et al. |
| 2004/0267282 A1 | 12/2004 | Shkarubo et al. |
| 2005/0021123 A1 | 1/2005 | Dorn et al. |
| 2005/0033402 A1 | 2/2005 | Cully et al. |
| 2005/0033403 A1 | 2/2005 | Ward et al. |
| 2005/0060016 A1 | 3/2005 | Wu et al. |
| 2005/0060018 A1 | 3/2005 | Dittman |
| 2005/0080476 A1 | 4/2005 | Gunderson et al. |
| 2005/0085890 A1 | 4/2005 | Rasmussen et al. |
| 2005/0090834 A1 | 4/2005 | Chiang et al. |
| 2005/0090890 A1 | 4/2005 | Wu et al. |
| 2005/0113902 A1 | 5/2005 | Geiser et al. |
| 2005/0131514 A1 | 6/2005 | Hijlkema et al. |
| 2005/0149159 A1 | 7/2005 | Andreas et al. |
| 2005/0177246 A1 | 8/2005 | Datta et al. |
| 2005/0182475 A1 | 8/2005 | Jen et al. |
| 2005/0209670 A1 | 9/2005 | George et al. |
| 2005/0209685 A1 | 9/2005 | Shifrin et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0004433 A1 | 1/2006 | Greenberg et al. |
| 2006/0009858 A1 | 1/2006 | Levine et al. |
| 2006/0184224 A1 | 8/2006 | Angel |
| 2006/0184226 A1 | 8/2006 | Austin |
| 2008/0140178 A1* | 6/2008 | Rasmussen et al. ......... 623/1.11 |
| 2009/0024133 A1 | 1/2009 | Keady et al. |
| 2009/0030497 A1 | 1/2009 | Metcalf et al. |
| 2009/0099640 A1 | 4/2009 | Weng |
| 2010/0168834 A1 | 7/2010 | Ryan et al. |
| 2010/0262157 A1 | 10/2010 | Silver et al. |
| 2012/0172963 A1 | 7/2012 | Ryan et al. |
| 2012/0185031 A1 | 7/2012 | Ryan et al. |
| 2012/0221093 A1 | 8/2012 | McHugo |

FOREIGN PATENT DOCUMENTS

| | | |
|---|---|---|
| EP | 747 021 A2 | 12/1996 |
| EP | 1 525 859 A2 | 4/2005 |
| WO | WO 98/53761 A1 | 12/1998 |
| WO | WO 02/05885 A2 | 1/2002 |
| WO | WO 2005/107644 A1 | 11/2005 |
| WO | WO 2007/005799 A1 | 1/2007 |
| WO | WO 2007/022395 A1 | 2/2007 |
| WO | WO 2008/042266 A2 | 4/2008 |
| WO | WO 2008/098255 A2 | 8/2008 |
| WO | WO 2009/012061 A1 | 1/2009 |
| WO | WO 2010/040009 A1 | 4/2010 |
| WO | WO 2010/078352 A1 | 7/2010 |
| WO | WO 2011/094527 A1 | 8/2011 |
| WO | WO 2012/099731 A1 | 7/2012 |
| WO | WO 2012/099732 A1 | 7/2012 |
| WO | WO 2012/118638 A1 | 9/2012 |

OTHER PUBLICATIONS

Written Opinion completed Mar. 14, 2011 for International Application No. PCT/US2001/022903.

International Search Report and Written Opinion of the International Searching Authority for International Application No. PCT/US2008/069019, dated Oct. 17, 2008, 9 pages.

International Search Report and Written Opinion of the International Searching Authority for International Application No. PCT/US2009/069721, dated Feb. 19, 2010, 9 pages.

(56) References Cited

OTHER PUBLICATIONS

International Search Report and Written Opinion of the International Searching Authority for International Application No. PCT/US2011/022903, dated Mar. 24, 2011, 9 pages.

International Search Report and Written Opinion of the International Searching Authority for International Application No. PCT/US2012/020597, dated May 21, 2012, 11 pages.

International Search Report for International Application No. PCT/US2012/020598, dated May 10, 2012, 4 pages.

International Search Report and Written Opinion of the International Searching Authority for International Application No. PCT/US2012/025895, dated Jun. 6, 2012, 12 pages.

Albee, F., "Bone Surgery with Machine Tools," Scientific American, Apr. 1936, pp. 178-181.

\* cited by examiner

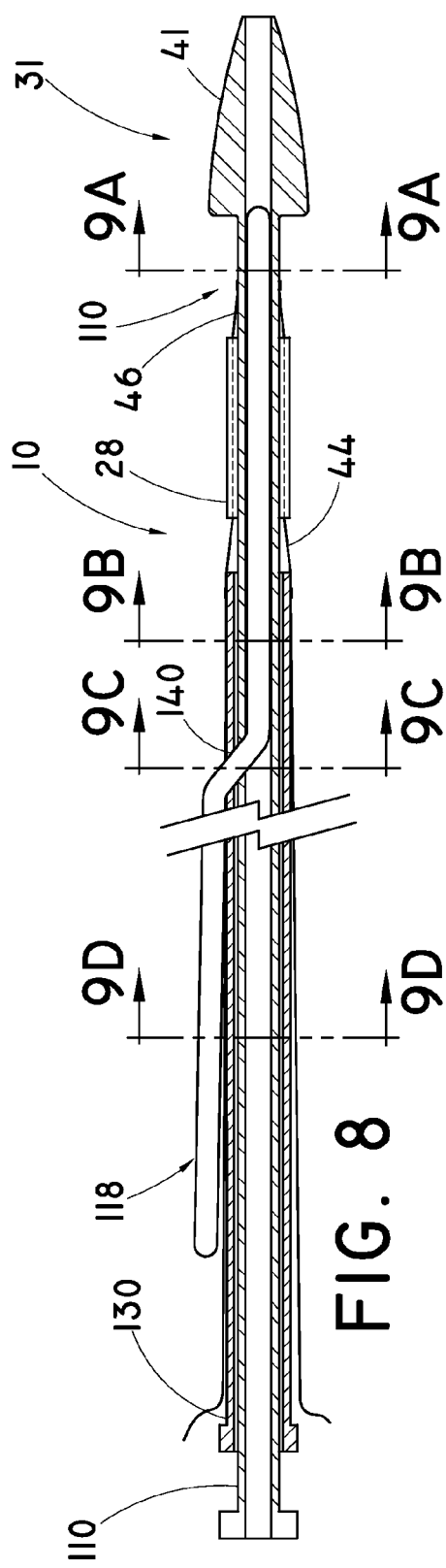
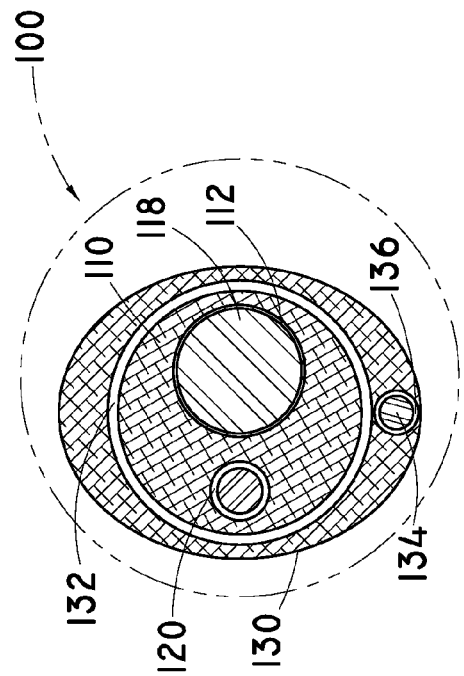
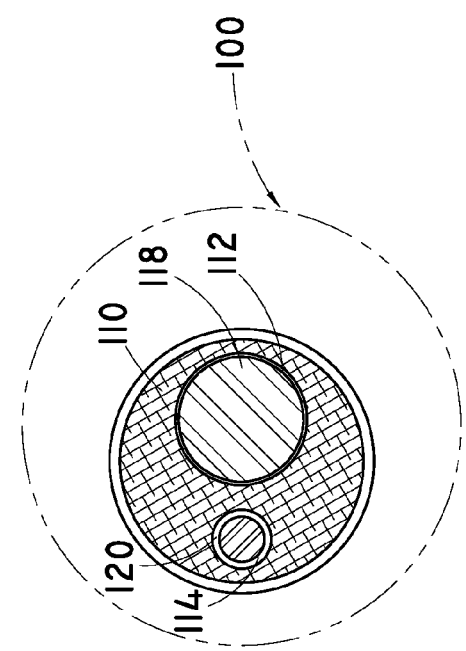

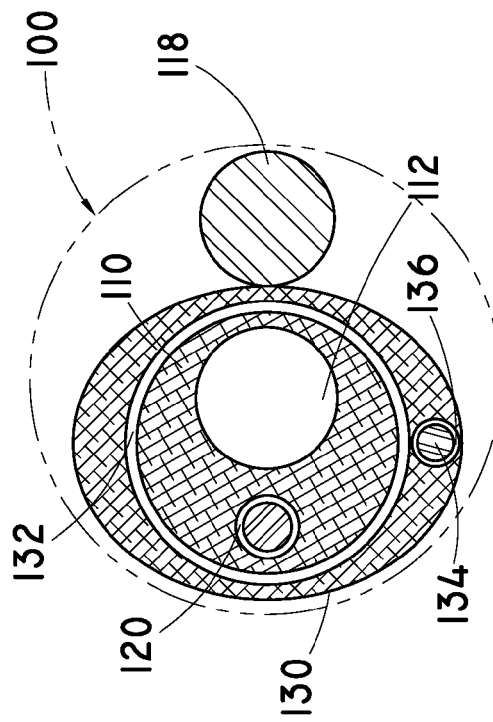
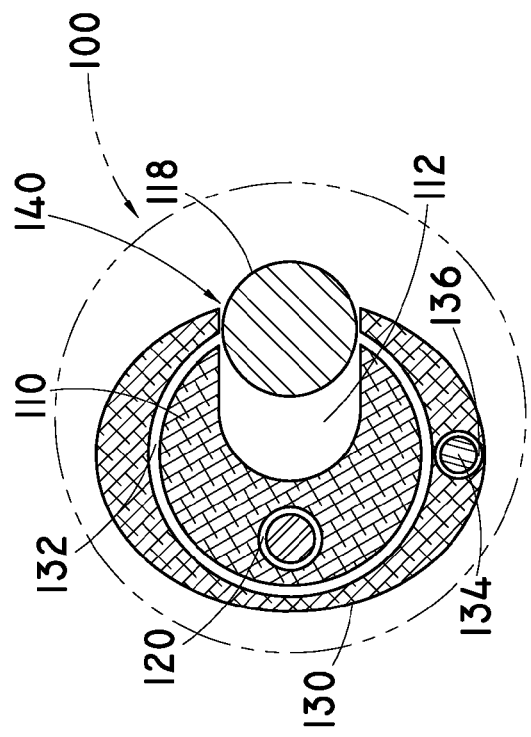

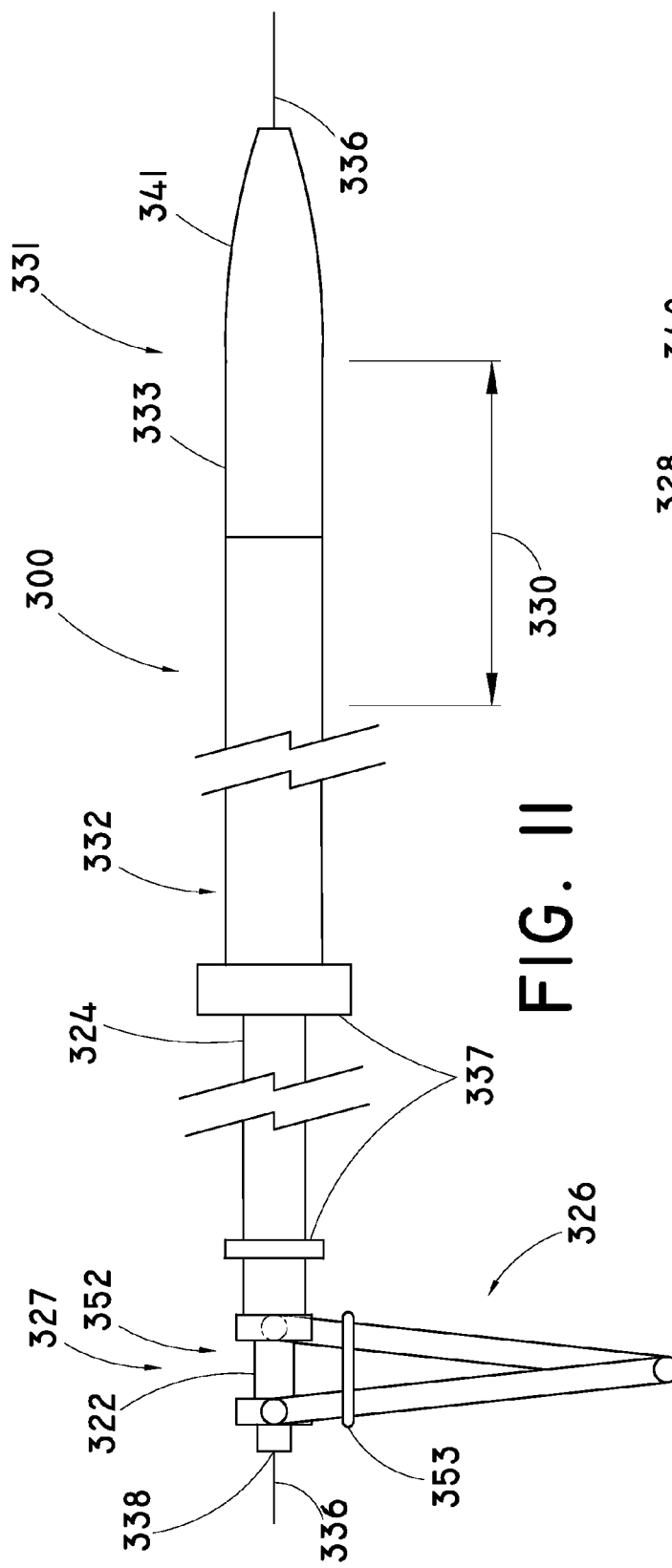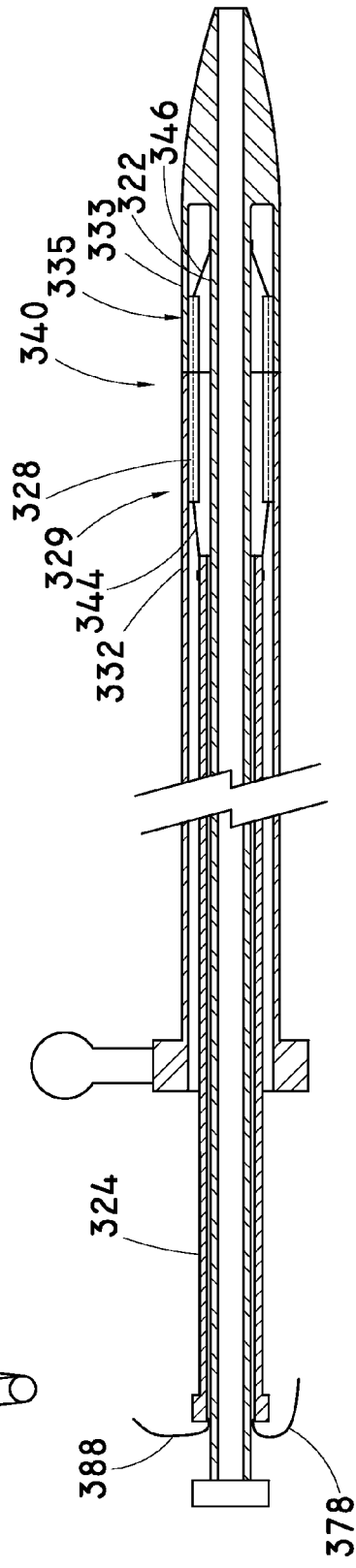
FIG. 11
FIG. 12

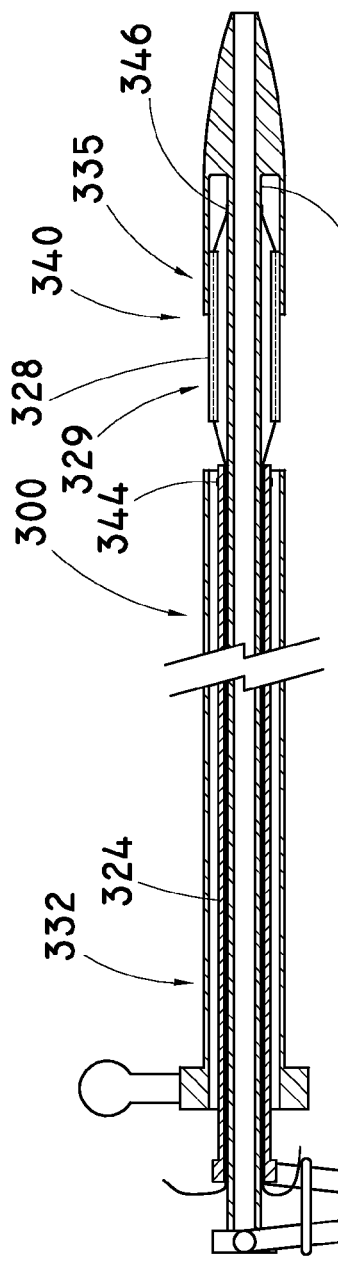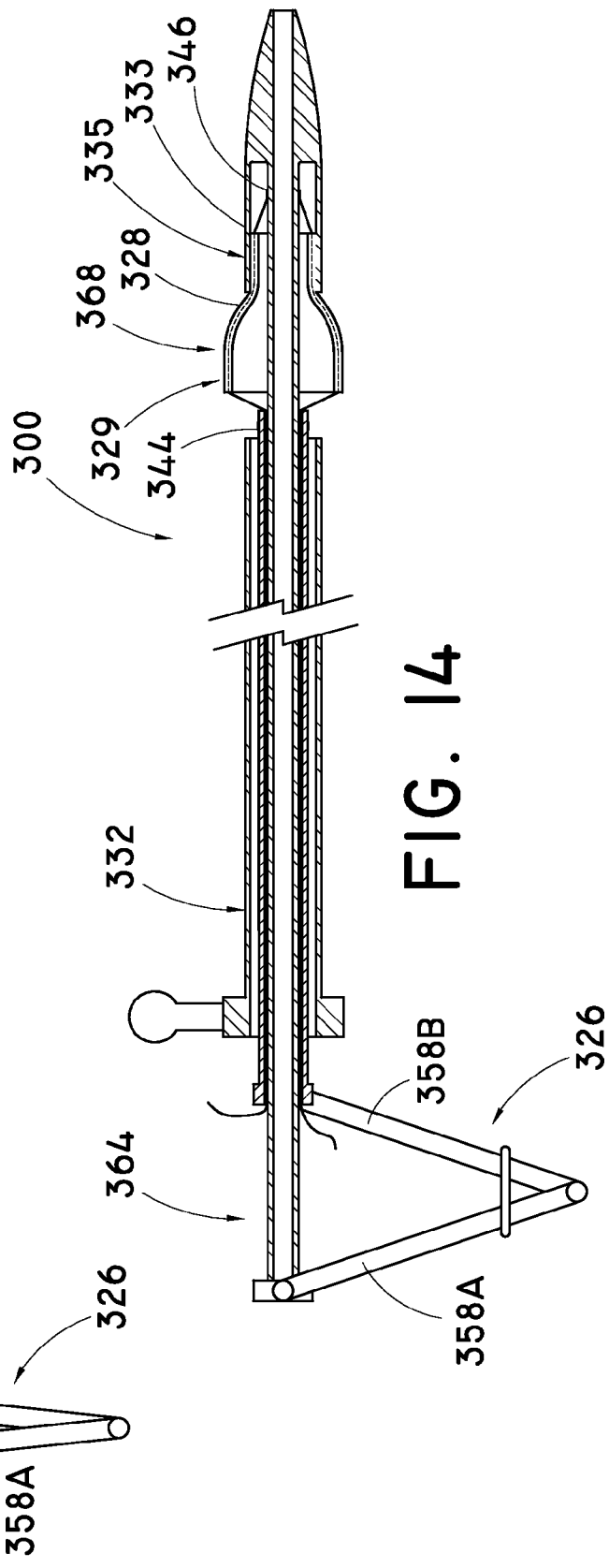

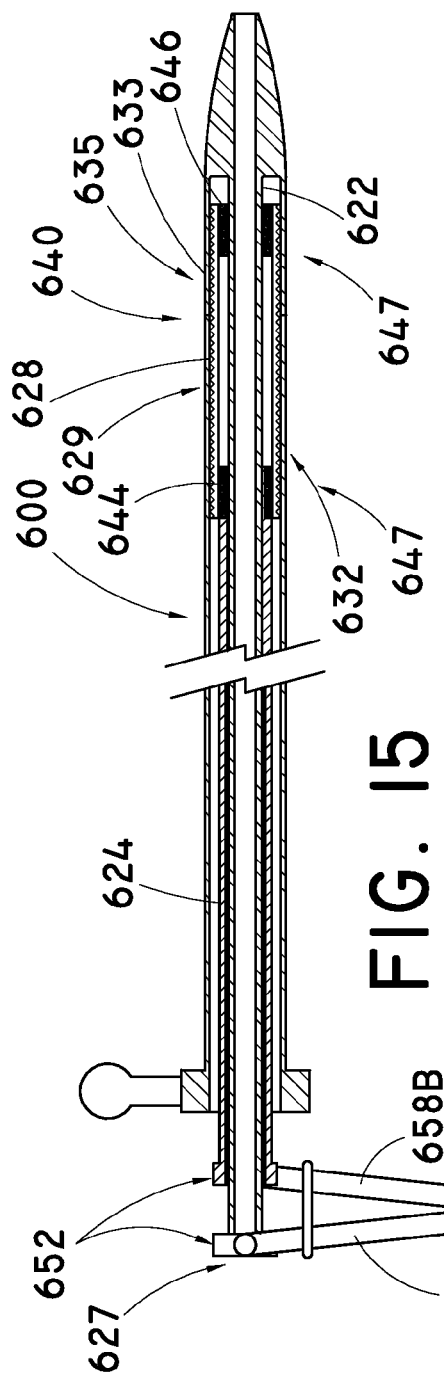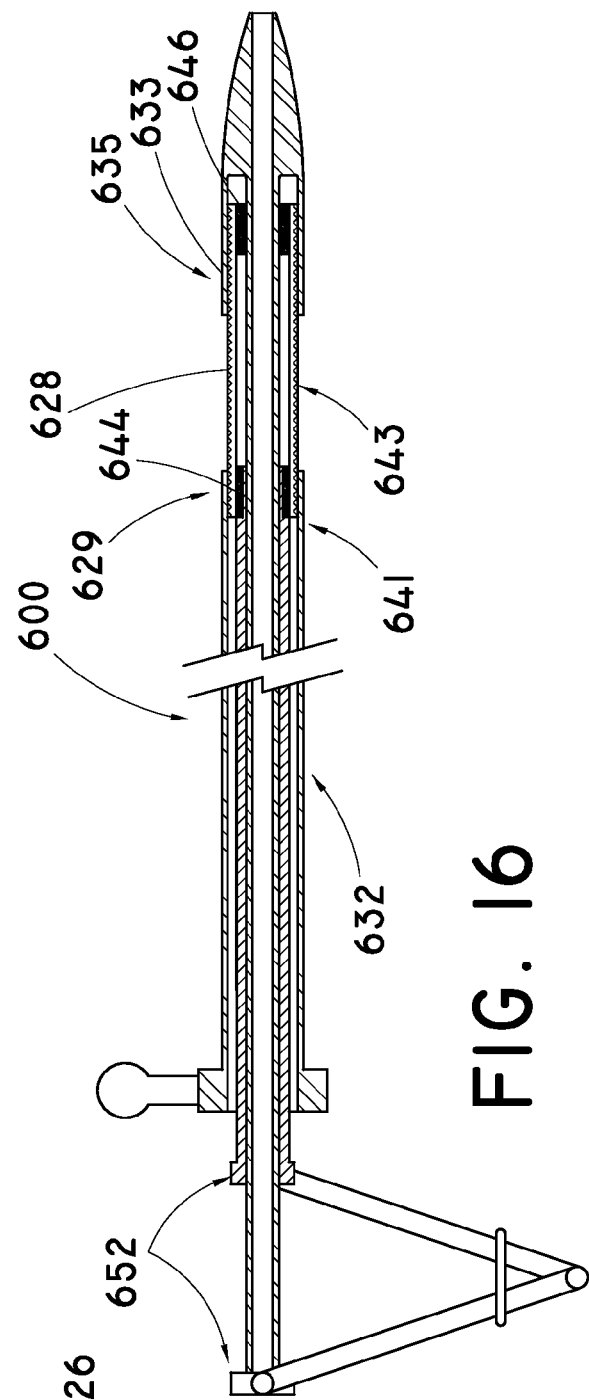

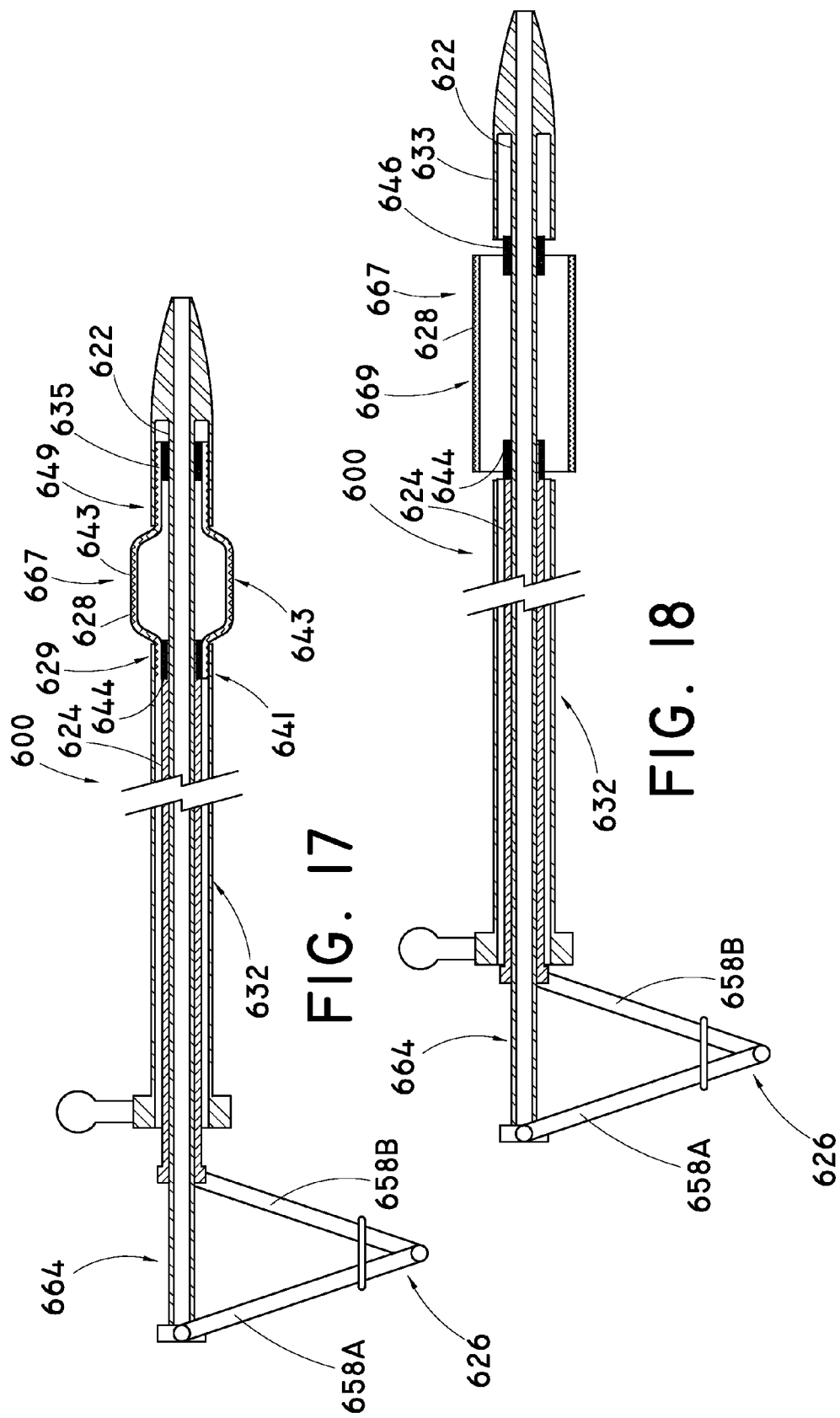

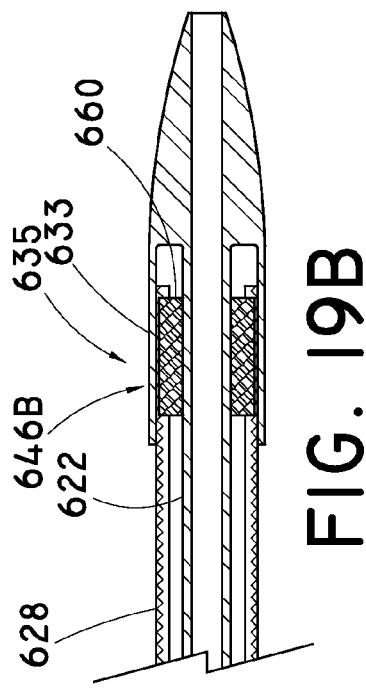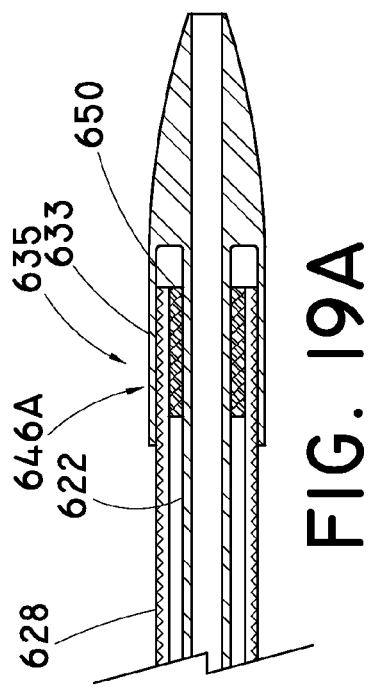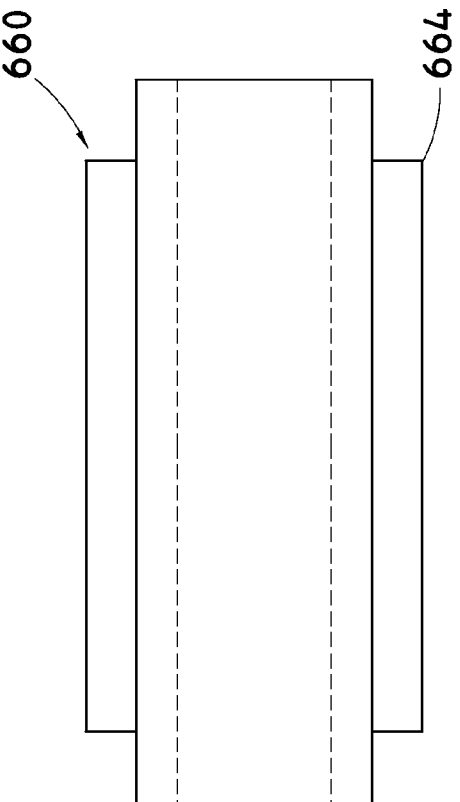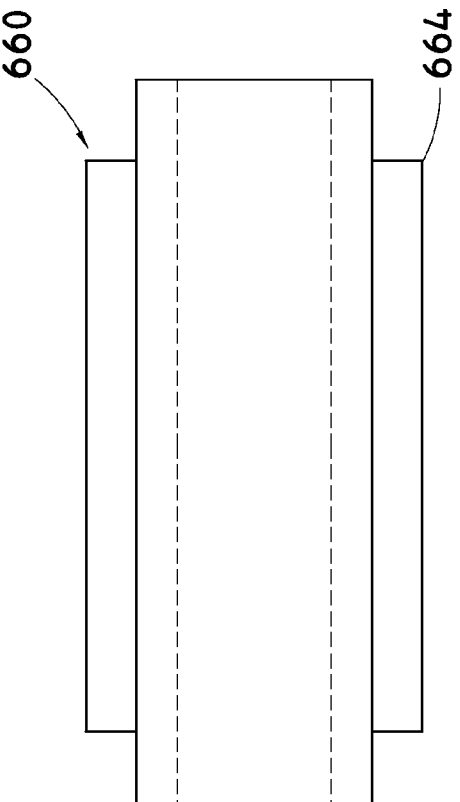

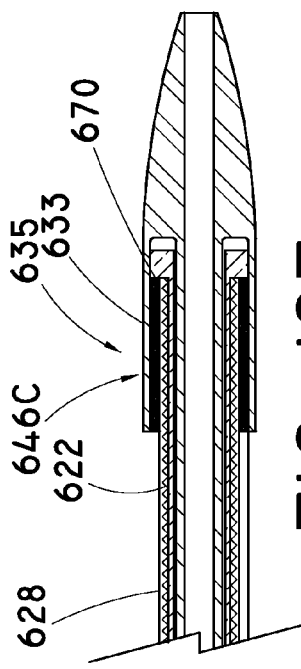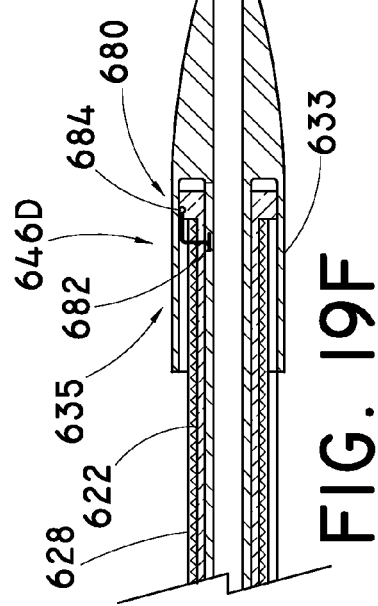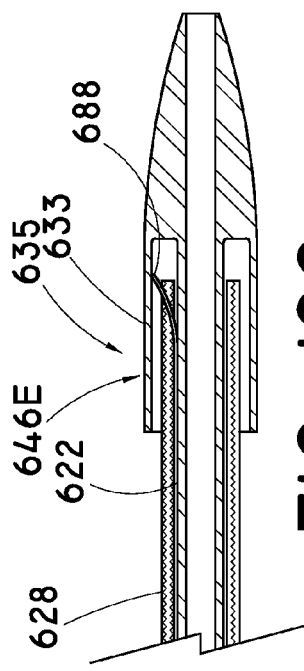

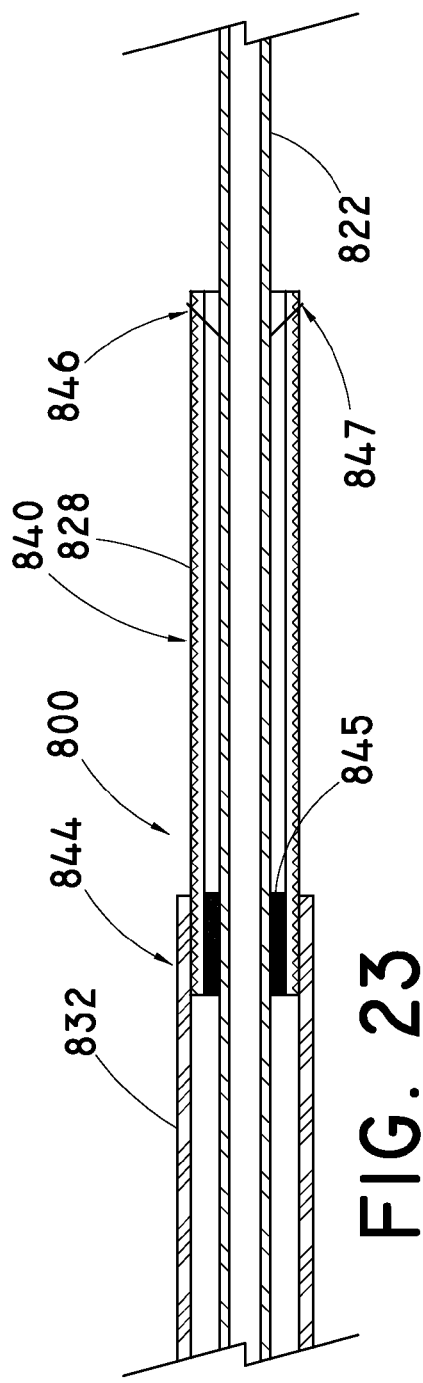
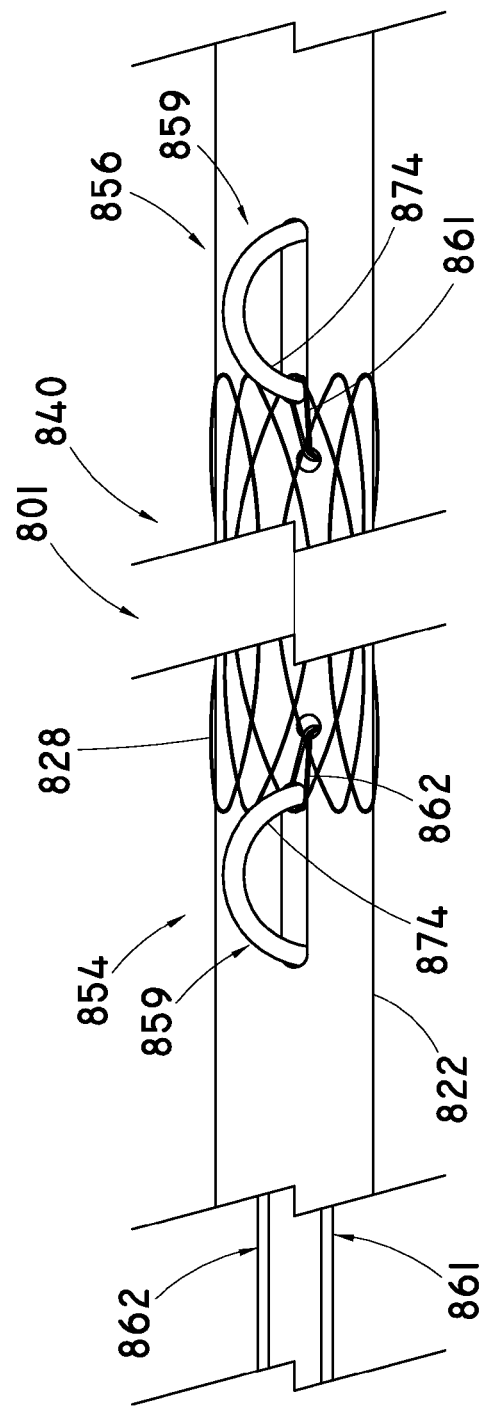
FIG. 23
FIG. 24

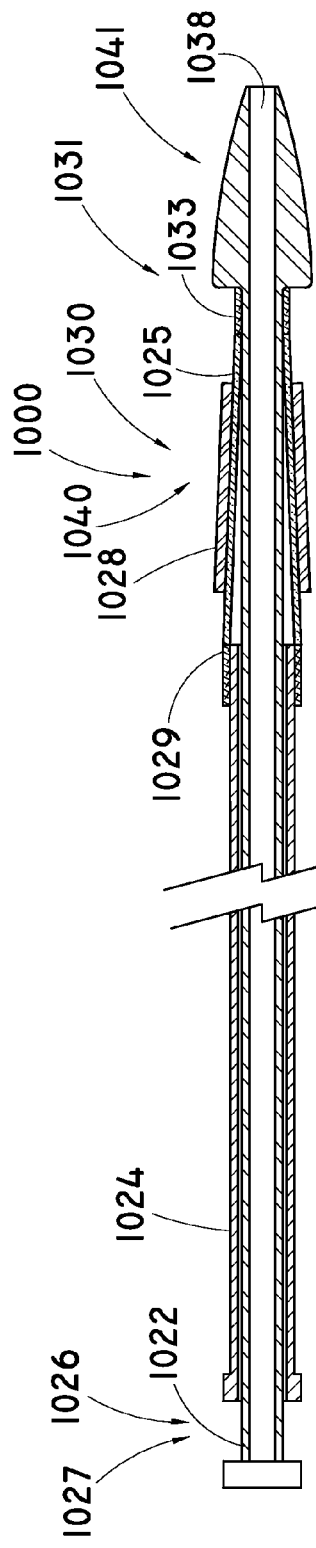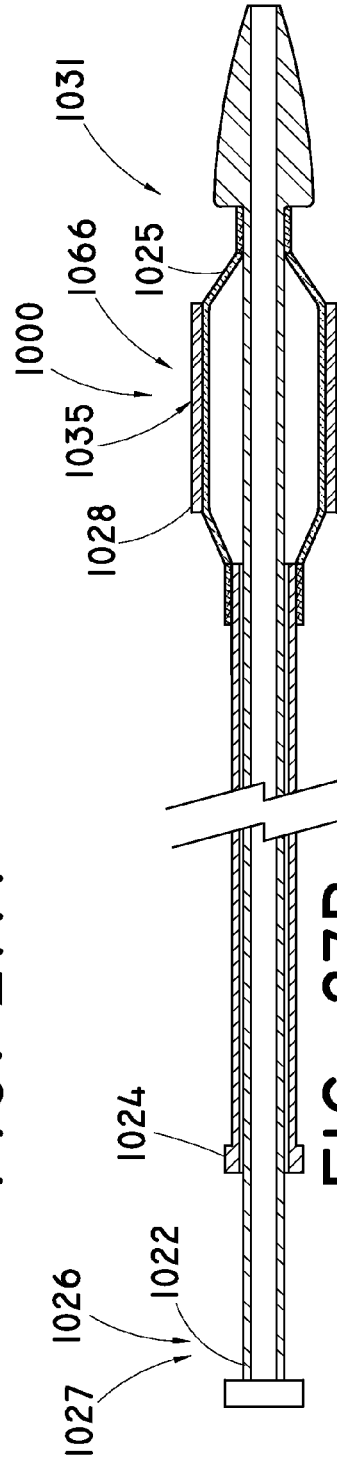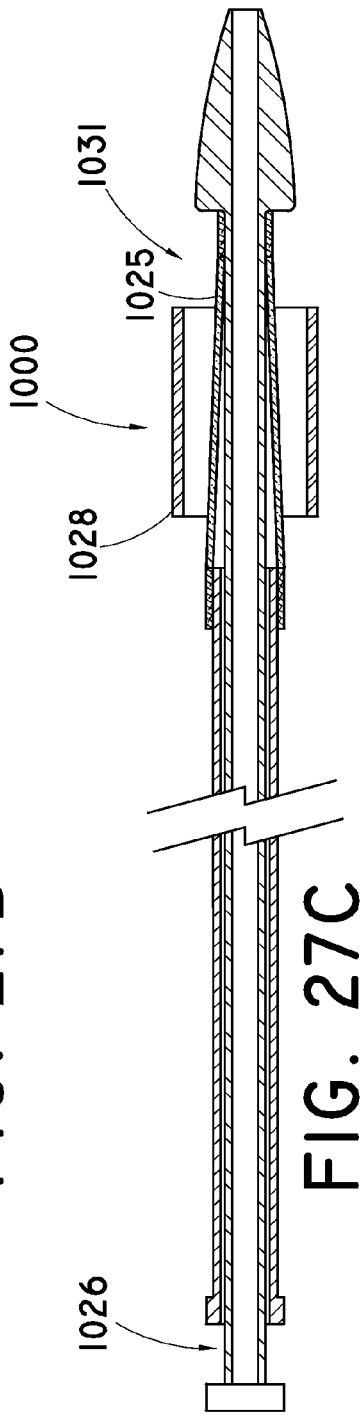

MECHANICALLY EXPANDABLE DELIVERY AND DILATION SYSTEMS

RELATED APPLICATIONS

This application claims the benefit under 35 U.S.C. §119 (e) of U.S. Application Ser. No. 61/299,605, filed Jan. 29, 2010, which is hereby incorporated by reference in its entirety.

TECHNICAL FIELD

This invention relates to a medical device and, in particular to a mechanically expandable device for delivering and deploying a stent or dilation and a method of delivering and deploying the stent into a body lumen.

BACKGROUND

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling back the outer sheath relative to the inner catheter until the stent is exposed. The self-expanding stent expands from the stent distal end to the stent proximal end as the sheath is proximally withdrawn.

Several problems may occur with the sheathed delivery device described above. The sheath release delivery devices are difficult to reposition or remove and slow to operate. The stent may only be partially deployed prior to reconstrainment of the stent by the sheath in order to still reposition or remove the stent. Once the stent is fully deployed, i.e. radially expanded, the sheath cannot reconstrain the stent. For example, utilizing a conventional outer sheath/inner catheter delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded into the body lumen. Additionally, retraction of the outer sheath may not be achieved with controlled movement because the physician is manually retracting the outer sheath which may lead to uneven or inadvertent jerking back of the outer sheath that can lead to improper positioning of the stent.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications, for example to prevent stent migration or to properly open a stricture along the entire length of the stricture. An additional drawback occurs with the sheathed stent delivery system where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catchers and hysterics in the movement of the stent. The sheathed stent delivery device also requires more space within an endoscope compared to a sheathless device and also adds additional expense to the delivery system.

Accordingly, in view of the drawbacks of current technology, there is a desire for a mechanically expandable delivery system and dilation system that can increase the control, accuracy and ease of placement of a stent during deployment of the stent within a patient or dilation of a lumen within a patient. The delivery system would ideally reduce the risk of malfunction while providing for a smoother, more accurate and quicker deployment of the entire stent. The delivery system also would provide the ability to reconstrain, recapture, reposition and/or remove the stent after expansion of the stent.

SUMMARY OF THE INVENTION

Accordingly, it is an object of the present invention to provide a device and a method having features that resolve or improve on one or more of the above-described drawbacks.

The foregoing object is obtained in one aspect of the present invention by providing a stent delivery system. The stent delivery system includes an elongate shaft including a proximal portion, a distal portion, a lumen extending at least partially therethrough, and a stent receiving portion on the distal portion of the shaft. The stent delivery system also includes a stent positioned at the stent receiving portion of the elongate shaft, the stent having a constrained configuration and an expanded configuration. A proximal constraining member and a distal constraining member releasably connected to the stent and having a first position and a second position are also included. The proximal constraining member and the distal constraining member cooperatively apply a longitudinal tensile force to at least a portion of the stent in the constrained configuration with the proximal and distal constraining members each in the first position.

In another aspect of the present invention, a method for implanting a stent using a stent delivery system is provided. The method includes inserting a distal portion of a stent delivery system into the lumen of a patient. The stent delivery system includes an elongate shaft including a proximal portion, a distal portion, a lumen extending at least partially therethrough, and a stent receiving portion on the distal portion of the shaft. The stent delivery system also includes a stent positioned at the stent receiving portion of the elongate shaft, the stent having a constrained configuration and an expanded configuration, and a proximal constraining member releasably connected to the stent and having a first position and a second position and a distal constraining member releasably connected to the stent and having a first position and a second position. The method further includes holding the stent in the constrained configuration with a longitudinal tensile force applied to the stent by the proximal and distal constraining members each in the first position and cooperatively tensioning the stent for delivery of the stent to the implant site, positioning the stent at the implant site and expanding the stent to the expanded configuration by moving the proximal and distal constraining members each to the second position and releasing longitudinal tensile force on the stent.

In another aspect of the present invention, a system is provided. The system includes an inner elongate shaft including a proximal portion, a distal portion and a lumen extending at least partially therethrough and an outer elongate shaft including a proximal portion, a distal portion and a lumen extending at least partially therethrough. The inner elongate shaft coaxially extends at least partially within the lumen of the outer elongate shaft and the inner and outer elongate shafts are movably positionable relative to each other. The system also includes an expandable member having a first end portion and a second end portion and having a constrained configuration and an expanded configuration. The first end portion is operably connected to one of the inner and the outer elongate shaft and the second end portion is operably connected to the other of the inner and the outer elongate shaft. Movement of the inner and outer elongate shafts relative to each other in a first direction applies opposing longitudinal force to at least a portion of the expandable member and movement of the inner and outer elongate shafts relative to each other in a second direction releases the longitudinal force on the at least a portion of the expandable member.

BRIEF DESCRIPTION OF THE DRAWINGS

FIG. 8 is a partial view of a distal portion of a delivery system according to the present invention;

FIGS. 9A-9D are cross sectional views through the delivery system shown in FIG. 8;

FIG. 11 is a side view of an alternative embodiment of a delivery system according to the present invention;

FIG. 12 is a sectional view of the device shown in FIG. 11 showing the stent in a constrained configuration;

FIG. 13 is a sectional view of the device shown in FIG. 12 with a proximal outer sheath withdrawn and the stent in a constrained configuration;

FIG. 14 is a sectional view of the device shown in FIG. 13 with the stent in an expanded configuration.

FIG. 15 is a sectional view of an alternative embodiment of a delivery system according to the present invention;

FIG. 16 is a sectional view of the device shown in FIG. 15 showing the stent in a constrained configuration and the proximal sheath withdrawn;

FIG. 17 is a sectional view of the device shown in FIG. 15 with a portion of the stent in an expanded configuration;

FIG. 18 is a sectional view of the device shown in FIG. 15 with the stent in an expanded configuration;

FIGS. 19A-19G illustrate alternative embodiments of a distal constraining member;

FIG. 23 is a partial view of an alternative embodiment of a stent delivery system;

FIG. 24 is a partial view of an alternative embodiment of a stent delivery system;

FIGS. 27A-27C illustrate an alternative embodiment of a stent delivery system.

DETAILED DESCRIPTION OF THE EMBODIMENTS

Figure 1:
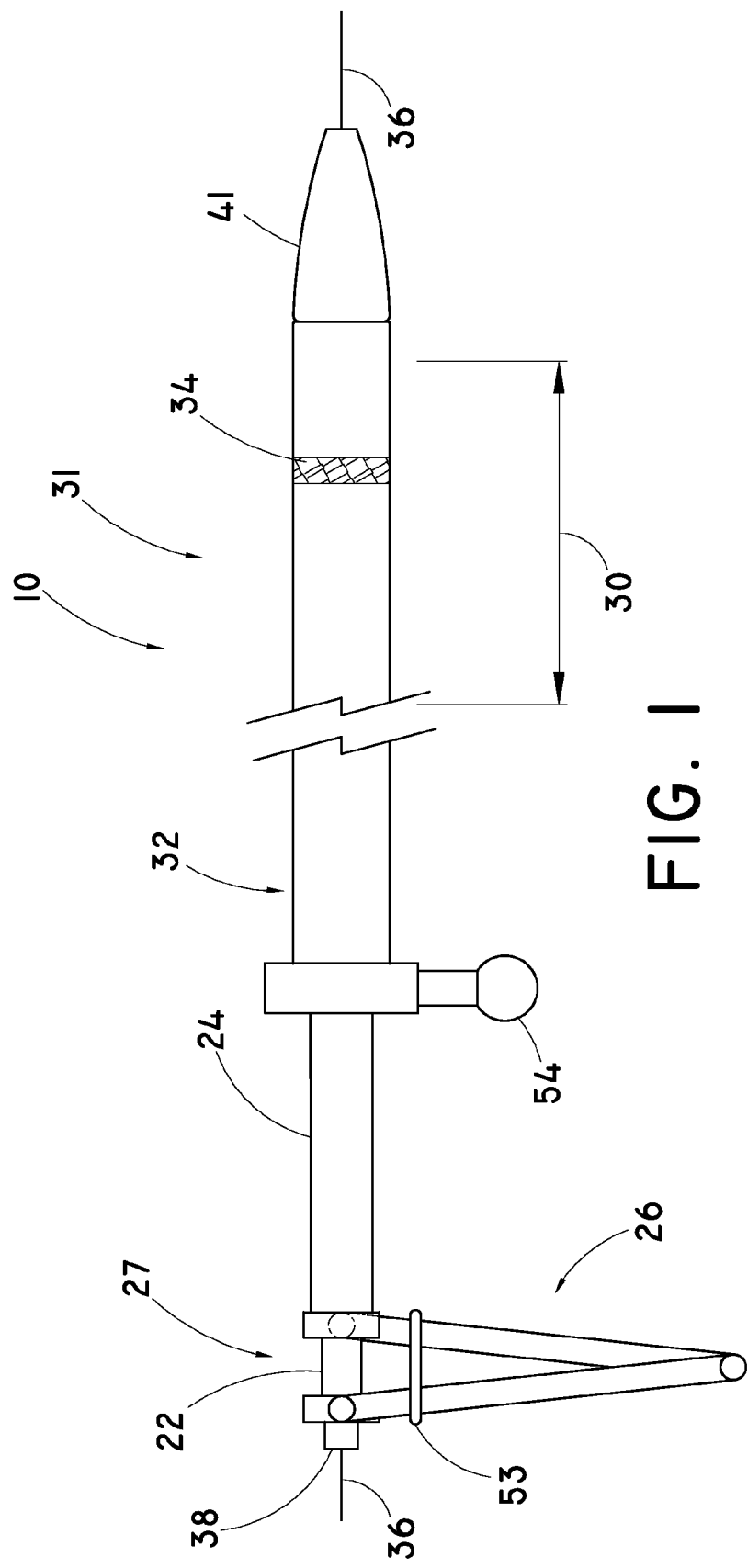
FIG. 1 is a side view of a stent delivery system according to an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the delivery system that is farthest from the physician and the term "proximal" means the portion of the delivery system that is nearest to the physician.

FIG. 1 illustrates a stent delivery system 10 for in accordance with embodiments of the present invention. The stent delivery system 10 includes an inner shaft 22, an outer shaft 24 and a handle 26 at a proximal portion 27 of the system 10. A stent 28 (shown in FIG. 2) is positionable on a stent region 30 of the inner shaft 22 at a distal portion 31 of the delivery system 10. The stent delivery system 10 may optionally include an outer sheath 32 slidably positionable over a portion of the outer shaft 24 and the inner shaft 22 to cover the stent region 30 and the stent 28. One or more radiopaque markers 34 may be included on the delivery system 10 to indicate the position of the stent 28. The stent delivery system 10 may also include a guidewire 36 extendable through a port 38 of the inner shaft 22 through a distal tip 41 at the distal portion 31 of the delivery system 10.

Figure 2:
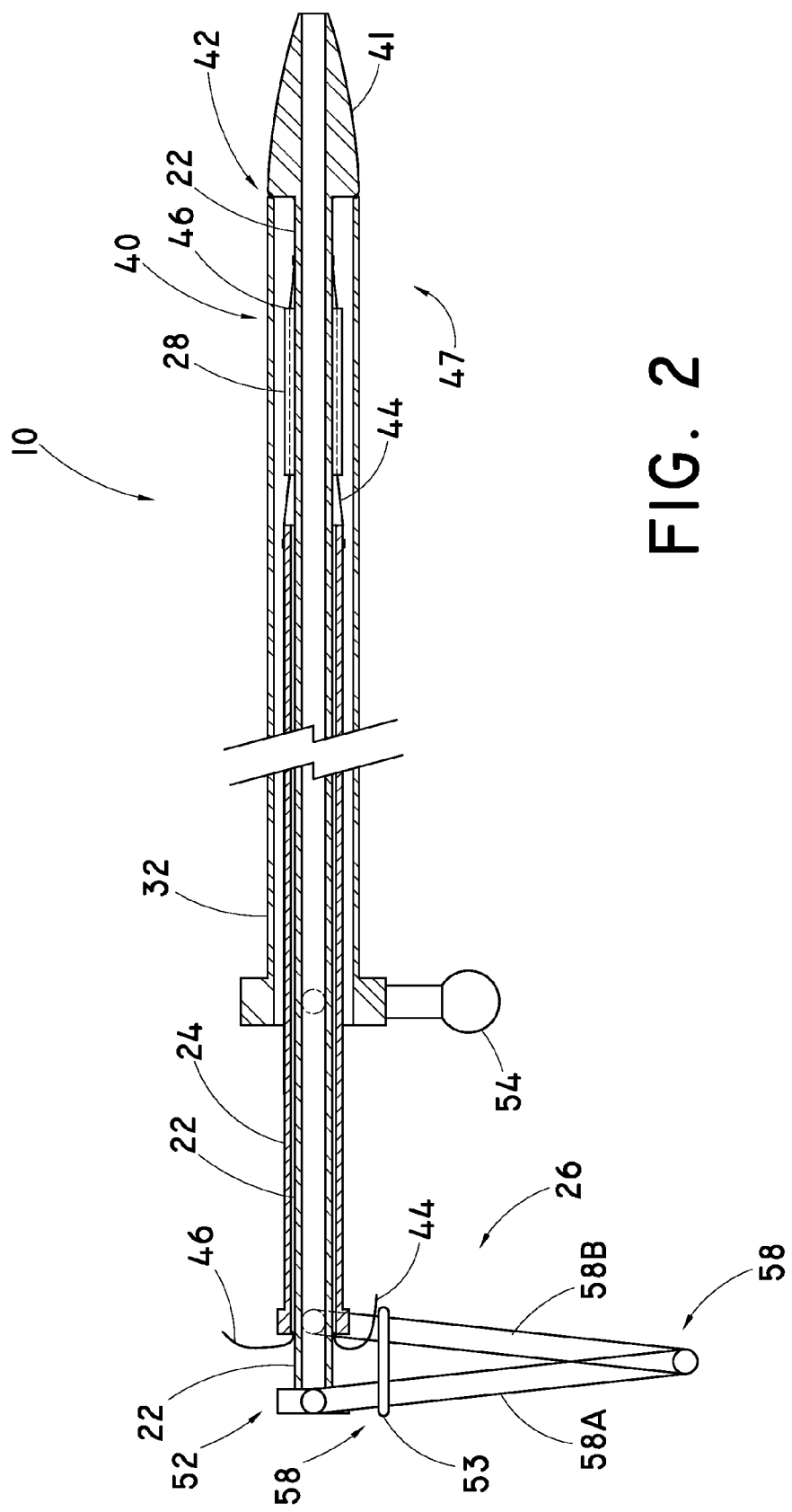
FIG. 2 is a sectional view of the device shown in FIG. 1 showing the stent in a constrained configuration.

FIG. 2 illustrates a sectional view of the stent delivery system 10 shown in FIG. 1. As shown in FIG. 2, the stent 28 is in a constrained configuration 40 collapsed against the inner shaft 22. In some embodiments, the stent 28 may be a self-expanding stent. The stent 28 may be any kind of stent that has a tendency to radially collapse when a longitudinal force is applied to the ends of the stent. By way of non-limiting example, the stent 28 may be formed as a woven mesh formed from a metal or polymer or a laser cut pattern formed in a metal stent. The stent may also be formed from a bioabsorbable material. One example of a woven stent is the EVOLUTION® stent (Wilson-Cook Medical, Inc.) The optional outer sheath 32 is shown extended distally over the stent 28 and abutting the distal tip 41 of the inner shaft 22 forming a smooth outer surface 42 of the delivery system 10. The outer sheath 32 is operably connected to the handle 26. The outer sheath 32 may be provided to facilitate a smoother delivery of the system 10 through a bodily lumen of the patient. The stent 28 is held in the constrained configuration 40 by a different mechanism that may be provided with or without the outer sheath 32, an embodiment of which is described in detail below with reference to FIGS. 5A-5C, that includes a proximal stent constraining member 44 and a distal stent constraining member 46 to longitudinally constrain the stent 28 and hold the stent 28 collapsed against the inner shaft 22. The proximal and distal stent constraining members 44, 46 are operably connected to the handle 26 by connection of the proximal constraining member 44 to the outer catheter 24 and the distal constraining member 46 to the inner catheter 22. When present, the outer sheath 32 may provide some compressive force to the stent in addition to the proximal and distal constraining members 44, 46. The handle 26 is shown FIG. 2 in a closed position 52. The handle 26 may include a lock 53 to releasably lock the handle 26 in the closed position 52.

Figure 3:
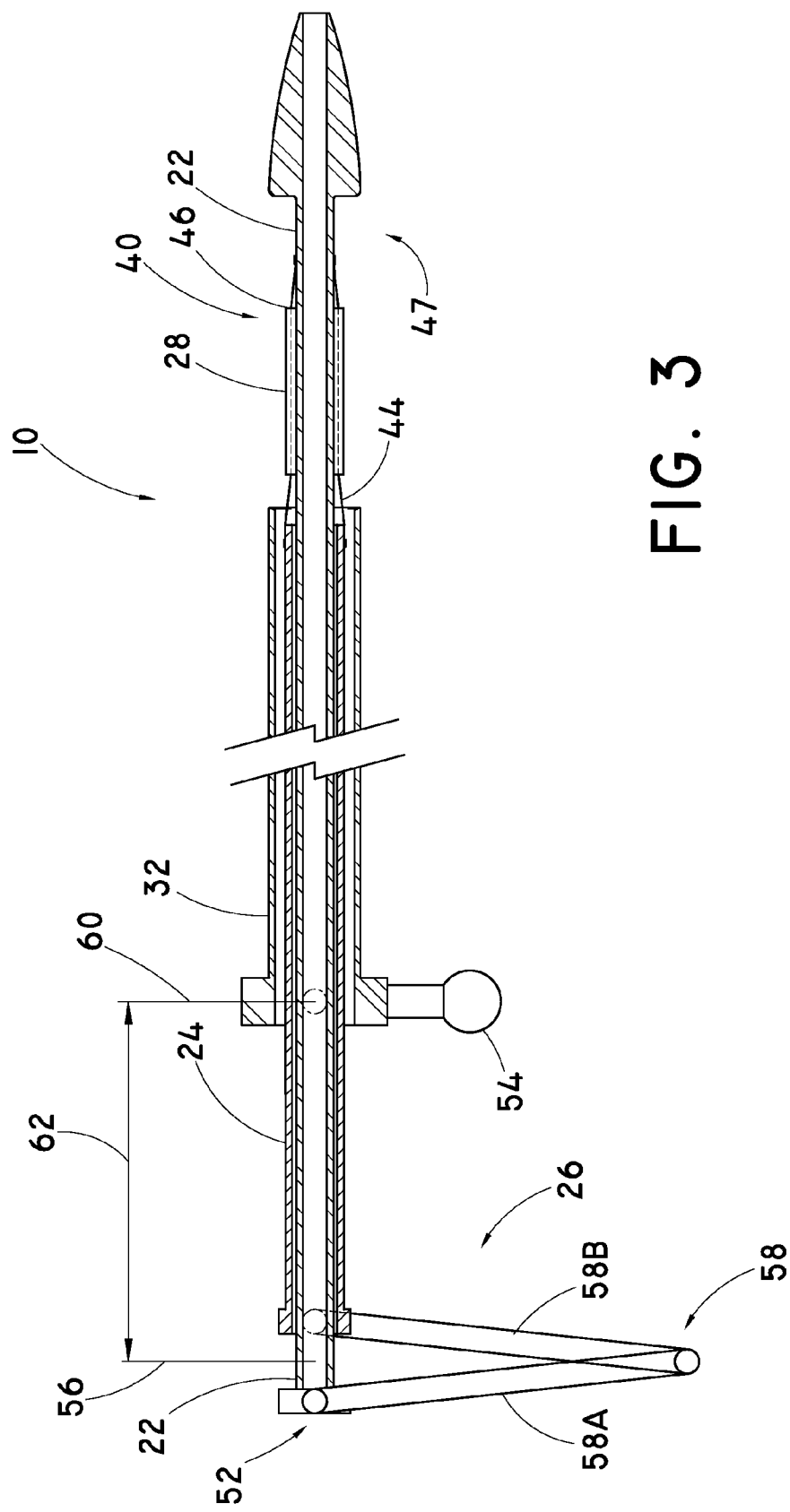
FIG. 3 is a sectional view of the device shown in FIG. 2 with an outer sheath withdrawn and the stent in a constrained configuration.

As shown in FIG. 3, the outer sheath 32 has been proximally pulled back completely exposing the stent 28 in the constrained configuration 40 on the inner shaft 22. The outer sheath 32 may be releasably locked against the handle 26 to keep the sheath 32 stationary relative to the handle 26. The stent 28 is held compressed against the inner shaft 22 by the proximal and distal stent constraining members 44, 46 in a first position 47 applying longitudinal force to the stent 28 in opposite directions. The handle 26 is in the closed position 52 and the outer sheath 32 has manually been pulled proximally away from the stent region 30 of the inner shaft 22 and anchored to the sheath controlling portion 54 of the handle 26 to expose the stent 28 (see FIG. 1 illustrating stent region 30). The handle 26 further includes a proximal handle portion 58 that is operably connected to the inner shaft 22 and the outer shaft 24 to move the inner and outer shafts 22, 24 relative to each other as discussed below. The proximal handle portion 58 is movable between the closed position 52 (shown in FIG. 3) and an open position 64 (shown in FIG. 4). A midpoint 56 for attachment of the proximal handle portion 58 is shown for the handle 26. A second attachment midpoint 60 is shown for the sheath controlling portion 54. A distance 62 between the attachment midpoints 56, 60 remains constant when the proximal handle portion 58 is moved from the closed position 52 shown in FIG. 3 to the open position 64 shown in FIG. 4.

Figure 4:
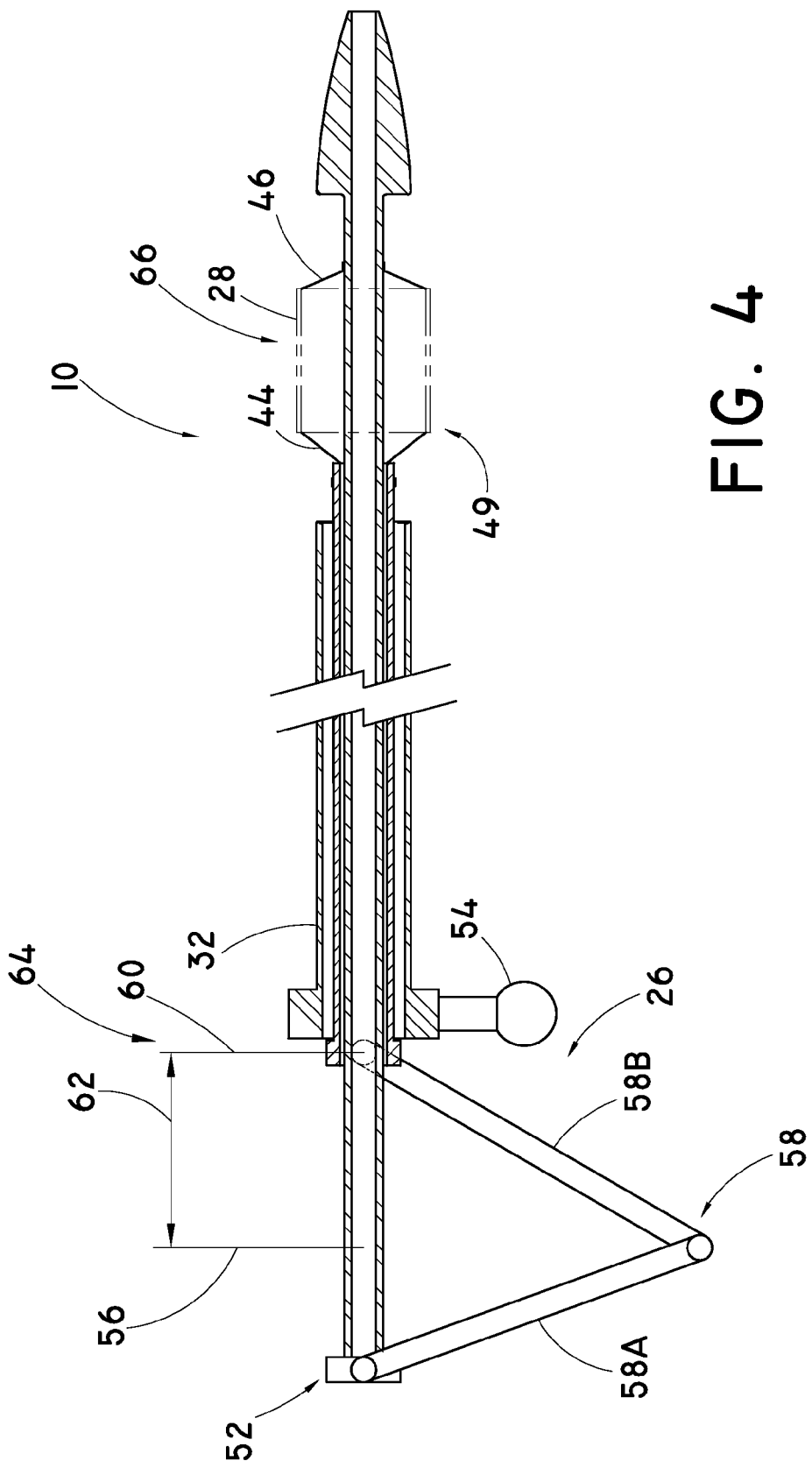
FIG. 4 is a sectional view of the device shown in FIG. 3 with the stent in an expanded configuration.

The stent 28 is shown in an expanded configuration 66 in FIG. 4 where the stent 28 is expanded away from the inner shaft 22. The proximal and distal constraining members 44, 46 are in a second position 49 and remain connected to the stent 28 but the longitudinal force on the stent 28 has been removed to allow the stent 28 to expand. The proximal portion 58 of the handle 26 has been moved to the open position 64 by expanding arms 58a, 58b of the proximal handle portion 58 in equal and opposite directions. The inner shaft 22 and the outer shaft 24 are moved in equal and opposite directions relative to each other by the proximal handle portion 58 and the proximal and distal constraining members 44, 46 are moved closer together. The stent 28 is released from the constrained configuration 40 to the expanded configuration 66 in response to the equal and opposite motion of the opening of the proximal handle portion 58 so that the release of the tension on the stent 28 is uniform within the patient's lumen. The proximal handle portion 58 may be spring loaded to facilitate the expansion of the arms 58a, 58b to the open position 64. The proximal handle portion 58 moves the inner shaft 22 relative to the outer shaft 24 so that the longitudinal tension exerted on the stent 28 by the proximal and distal constraining members 44, 46 is relaxed when the members 44, 46 are closer together and the stent 28 expands uniformly due to the uniform release of the tension on the stent 28 by the proximal and distal constraining members 44, 46.

As shown in FIG. 4, the proximal and distal constraining members 44, 46 remain connected to the stent 28 in the expanded configuration 66. The connection allows the stent 28 to be moved from the expanded configuration 66 with the outer sheath 32 completely removed from the stent 28 to the constrained configuration 40 so that the stent 28 is recollapsed onto the inner shaft 22 by moving the proximal handle portion 58 to the closed position 52. The proximal handle portion 58 moves the inner shaft 22 and the outer shaft 24 relative to each other so that the proximal and distal constraining members 44, 46 are spaced further apart and the longitudinal tension is returned to the stent 28 to collapse the stent onto the inner shaft 22. The stent 28 may be repeatedly moved between the constrained configuration 40 and the expanded configuration 66 by moving the proximal handle portion 58 between the closed position 52 and the open position 64 until the stent is properly positioned. With the stent repositioned in the constrained configuration 40, the outer sheath 32 may be repositioned over the stent 28 as shown in FIG. 2 and the stent 28 may even be withdrawn from the patient, for example if an incorrect size of stent was originally selected. The stent configurations may be changed multiple times within the patient for repositioning or removal until the proximal and distal constraining members 44, 46 are released from connection with the stent 28 as described below.

Figure 5A:
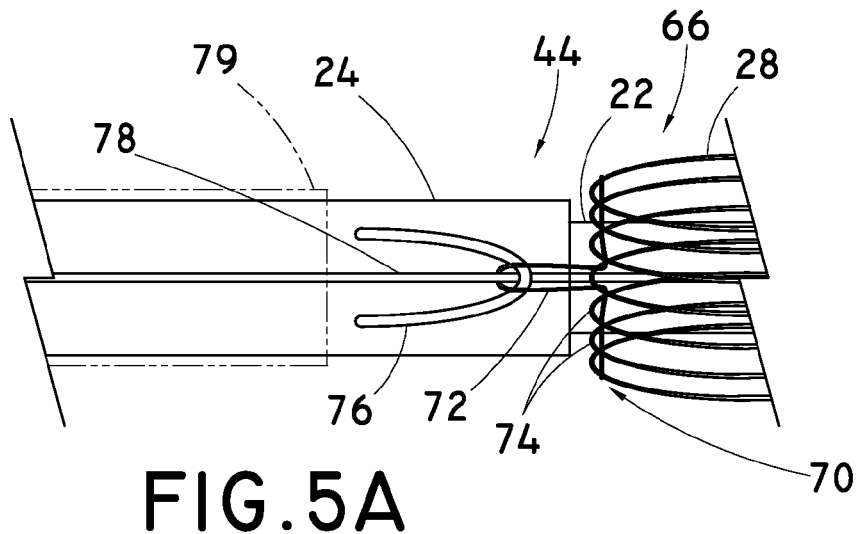
FIG. 5A is a partial side view of a proximal portion of the stent and the device shown in FIG. 4 illustrating a proximal constraining member.
Figure 5B:
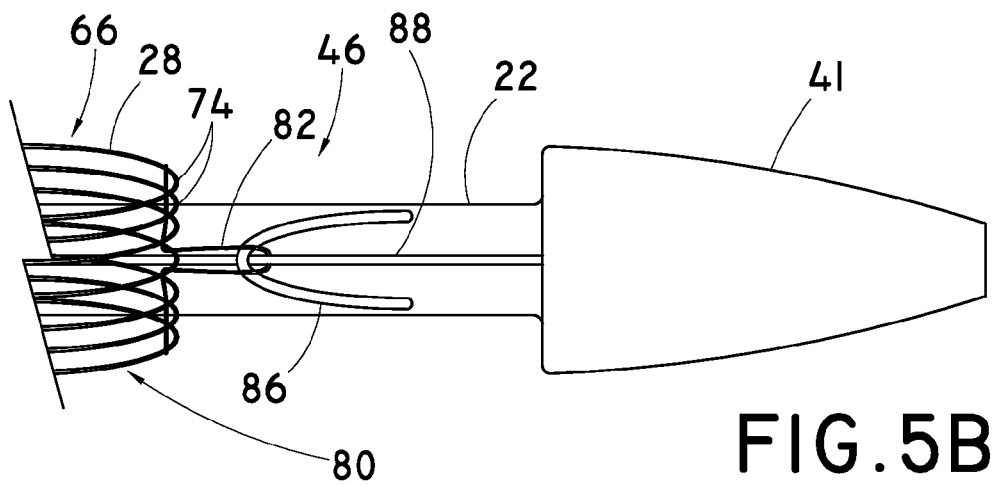
FIG. 5B is a partial side view of a distal portion of the stent and the device shown in FIG. 4 illustrating a distal constraining member.
Figure 5C:
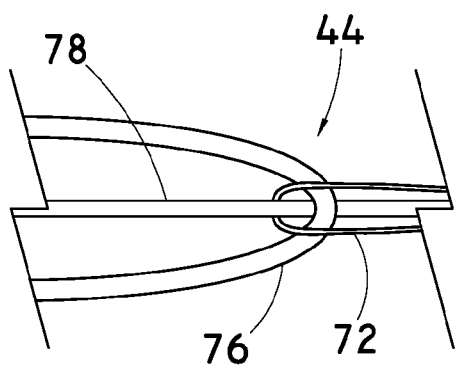
FIG. 5C is an enlarged view of a constraining member according to an embodiment of the present invention.

FIGS. 5A-5D illustrate an exemplary embodiment of the proximal constraining member 44 (FIG. 5A) and the distal constraining member (FIG. 5B). An exploded view of the components of the proximal constraining member 44 is shown in FIG. 5C and the components of the distal constraining member 46 may be a mirror image of the components of the proximal constraining member 44 (not shown). As shown in FIG. 5A, a proximal end portion 70 of the stent 28 remains connected to the inner shaft 22 even in the expanded configuration 66 using the proximal constraining member 44 in combination with the distal constraining member 46. The proximal constraining member 44 may include a first loop 72 that may be interwoven through one or more peaks 74 of the stent 28 so that the first loop 72 when pulled taught will collapse the peaks 74 of the stent 28 onto the inner shaft 22. The proximal constraining member 44 may further include a second retaining loop 76 that may be attached to the outer shaft 24. The proximal constraining member 44 may also include a proximal retaining wire 78 that is configured to cooperate with the first loop 72 and the second retaining loop 76 to releasably lock the first loop 72 to the second retaining loop 76 to allow selective expansion and contraction of the stent 28 when the proximal handle portion 58 is moved between the open position 64 and the closed position 52 in cooperation with the distal constraining member 46.

The first loop 72, the second loop 76 or both may be anchored at one or more points to better secure the stent 28 on the inner catheter 22, for example in a system 10 that is provided without a sheath. In some embodiments, the first loop 72 may be wound around the inner catheter 22 or the outer shaft 24 to facilitate holding the stent to the inner catheter 22 as the delivery system 10 is advanced to the treatment site through a curve, for example through an elevator of a duodenal endoscope. In some embodiments, the second loop 76 may be at least partially covered by a tubular member 79 as shown in dashed lines in FIG. 5A. The tubular member may be clear and may be made from any material known to one skilled in the art having suitable flexibility. By way of non-limiting example, the tubular member 79 may be made from PTFE.

An exemplary cooperative configuration of the proximal constraining member 44 is shown in FIG. 5C where a portion of the first loop 72 and the second retaining loop 76 are overlapping and the proximal retaining wire 78 extends through the overlapping loops 72, 76 to releasably hold the two loops 72, 76 together. The proximal retaining wire 78 shown in FIG. 5A may be frictionally engaged with a portion of the outer shaft 24 to hold the proximal retaining wire 78 in position until the stent 28 is in the proper position for release as discussed above. The proximal retaining wire 78 may be proximally withdrawn to release the proximal constraining member 44 and to completely release the stent 28 from connection to the inner shaft 22.

Figure 5D:
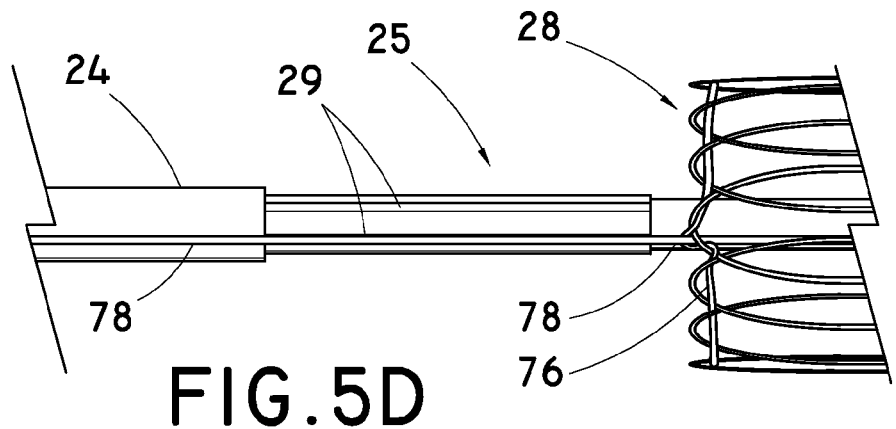
FIG. 5D is a partial side view of an embodiment of a proximal portion of the stent including a marker.

In some embodiments, the inner shaft 22 or the outer shaft or both may include a yellow endoscopic marker 25 that may be positioned close to the stent 28 to help the endoscopist position the stent. As shown in FIG. 5D, the marker 25 may include one or more slots 29 to receive the retaining wires 78. The slots 29 help to ensure that the wires 78 do not obscure the marker 25. The marker 25 may fill the entire inner diameter of the outer shaft 24 to make the marker 25 more visible. A similar marker 25 may also be positioned distal to the stent 28 (not shown).

As shown in FIG. 5B, a distal end portion 80 of the stent 28 may remain connected the inner shaft 22 even in the expanded configuration 66 using the distal constraining member 46. The distal constraining member 46 may include a first loop 82 that may be interwoven through one or more peaks 74 of the stent 28 so that the first loop 82 when pulled taught will collapse the peaks 74 of the stent 28 onto the outer shaft 24. The distal constraining member 46 may further include a second retaining loop 86 that may be attached to the inner shaft 22. The first loop 82, the second loop 86 or both may be anchored at one or more points to better secure the stent 28 on the inner catheter 22, for example in a system 10 that is provided without a sheath. In some embodiments, the first loop 82 may be wound around the inner catheter 22 or the outer shaft 24 to facilitate holding the stent to the inner catheter 22 as the delivery system 10 is advanced to the treatment site through a curve similar to the loop 72 described above.

The distal constraining member 46 may also include a distal retaining wire 88 that is configured to cooperate with the first loop 82 and the second retaining loop 86 to releasably hold the loops 82, 86 together to allow selective expansion and contraction of the stent 28 when the proximal handle portion 58 is moved between the open position 64 and the closed position 52. The distal retaining wire 88 may be frictionally engaged with the inner shaft 22 or the distal tip 41 to hold the distal retaining wire 88 in position until the stent 28 is properly positioned for release. The distal constraining member 46 may be configured similarly to the proximal constraining member 44 shown in FIG. 5C with the distal retaining wire 88 releasably locking the first loop 82 and the second retaining loop 86 together. The distal retaining wire 88 may be proximally withdrawn to release the distal constraining member 46 and to completely release the stent 28 from connection to the inner shaft 22.

The proximal and distal retaining wires 78, 88 may be connected to the handle 26 for proximal withdrawal from the loops 72, 76, 82, 86. The withdrawal of the proximal and distal retaining wires 78, 88 may be simultaneous or sequential. Because the stent 28 has been positioned in the proper position within the lumen of the patient by equal and opposite movement of the handle 26 to the open position 64 allowing the stent 28 to move to the expanded configuration 66, the timing of the release of the retaining wires 78, 88 is not critical for the positioning of the stent 28. As will be understood by one skilled in the art, the proximal constraining member 44 may be connected to the inner catheter 22 and the distal constraining member 46 may be connected to the outer catheter 24. In embodiments provided without the outer sheath 32, the peaks 74 of the stent 28 are collapsed closely against the inner catheter 22 at both ends of the stent 28 for delivery to the patient site.

While the proximal and distal restraining members 44, 46 have been described with reference to connection to the proximal and distal end portions 70, 80 of the stent 28, it is also possible to provide proximal and distal constraining members 44, 46 that are connected to other portions of the stent 28 and still provide a constrained configuration 40 for the stent 28. For example, the proximal constraining member may be connected to a mid proximal portion or mid-point of the stent and the distal constraining member may be connected to the distal end portion of the stent. Similarly, the proximal constraining member may be connected to the proximal end portion of the stent and the distal constraining member may be connected to the midpoint of mid distal portion of the stent or both the proximal and distal constraining members may be connected to other than the proximal and distal end portions of the stent. In some embodiments, the proximal or the distal constraining members or both proximal and distal constraining members may be connected to the stent at a plurality of positions on the stent.

Figure 6A:
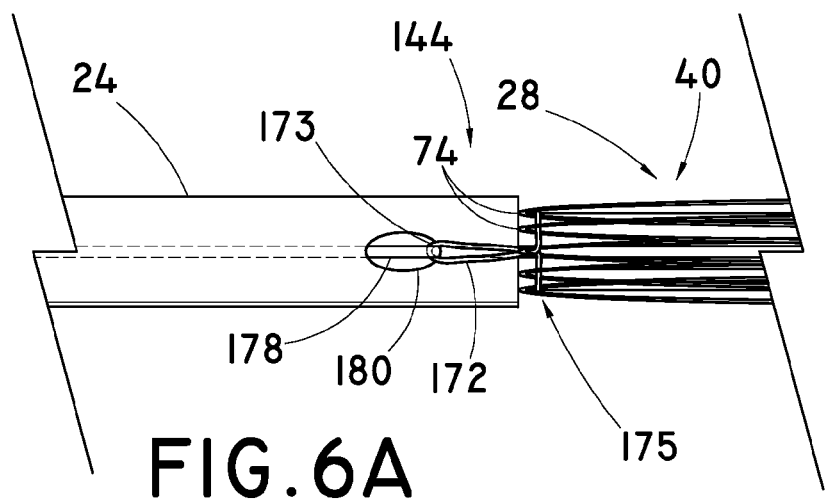
FIG. 6A is a partial side view of an alternative embodiment of a proximal constraining member.
Figure 6B:
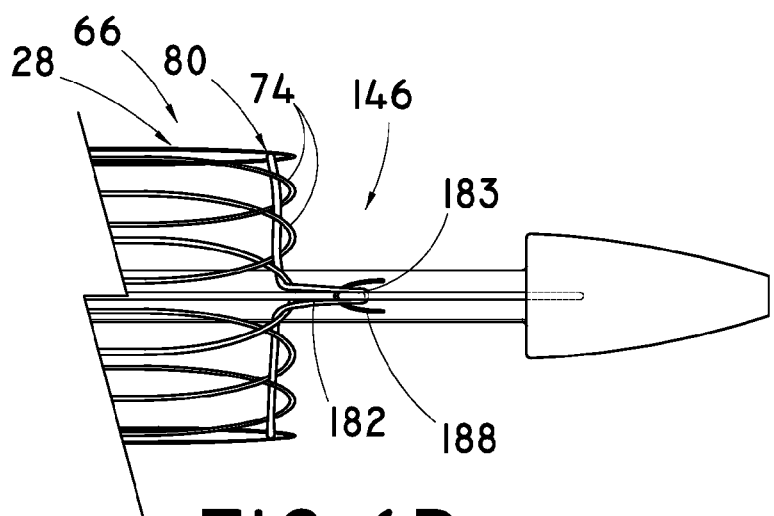
FIG. 6B is a partial side view of an alternative embodiment of a distal constraining member.
Figure 6C:
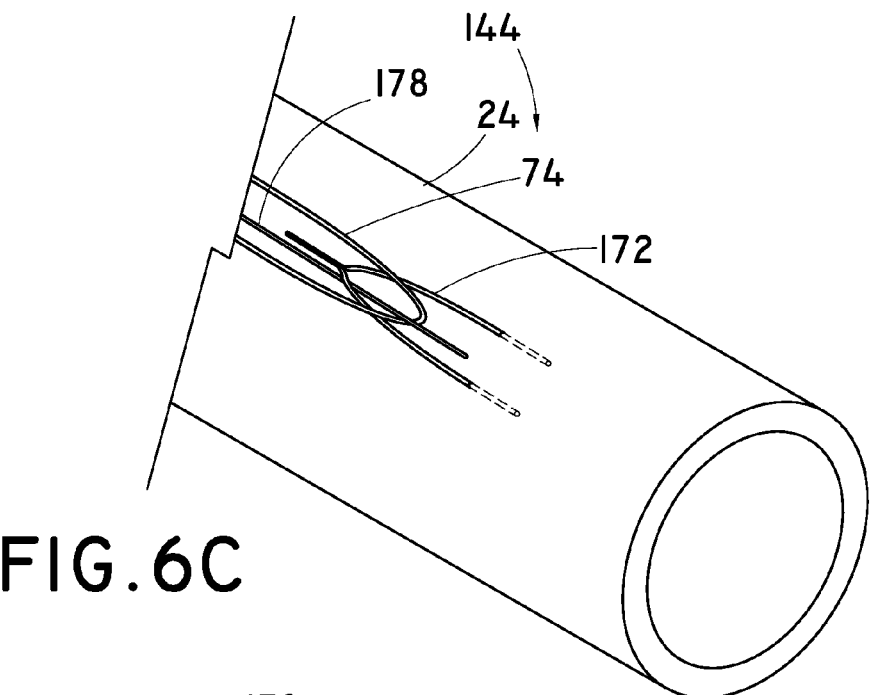
FIG. 6C is an enlarged view of an alternative embodiment of a constraining member.
Figure 6D:
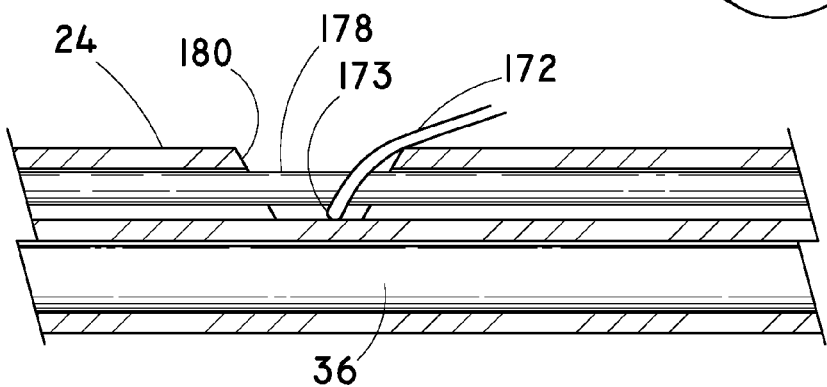
FIG. 6D is a partial sectional view of a constraining member.

In some embodiments, the stent delivery system 10 may be provided with a proximal constraining member 144 and a distal constraining member 146 as shown in FIGS. 6A and 6B. Similar to the proximal and distal constraining members 44, 46 described above the proximal and distal constringing members 144, 146 cooperatively apply and release tensioning force on the stent 28 in connection with the handle 26. The proximal constraining member 144 is shown in FIG. 6A with stent 28 in the constrained configuration 40. The proximal constraining member 144 includes a first loop 172 and a proximal retaining wire 178. The first loop 172 may be connected to the outer catheter 24. By way of non-limiting example, one portion 173 of the first loop 172 may be connected to the outer catheter 24 through an opening 180 in the outer catheter 24 so that the portion 173 of the loop 172 is constrained under the proximal retaining wire 178 as shown in FIGS. 6A and 6D. The first loop 172 may also be connected to the outer catheter 24 by welding, gluing, bonding or other fastening method known to one skilled in the art as shown in FIG. 6C. Another portion 175 of the first loop 172 may be woven through one or more peaks 74 of the stent 28 so that the first loop 172 when pulled taught will collapse the peaks 74 of the stent 28 onto the inner shaft 22 as described above. The proximal constraining member 144 may also include a proximal retaining wire 178 that cooperatively engages a portion of the first loop 172 to releasably hold the first loop 172 on the stent 28 to allow the stent 28 to be expanded and collapsed repeatedly for proper positioning within the patient's lumen. The proximal retaining wire 178 may be proximally withdrawn from the first loop 172 to release the stent 28 from connection with the proximal constraining member 144. The first loop 172 may be withdrawn with the device 10 from the patient and released from the stent 28.

The distal constraining member 146 is shown in FIG. 6B with stent 28 in the expanded configuration 66. The distal constraining member 146 includes a first loop 182 and a distal retaining wire 188. A portion 183 of the first loop 182 may be connected to the inner catheter 22 in a similar manner to the first loop 172 of the proximal constraining member 144 described above. Another portion 185 of the first loop 182 may be woven through one or more peaks 74 at the distal end 80 of the stent 28 so that when the first loop 182 of the distal constraining member 146 is pulled taught will collapse the peaks 74 of the stent 28 onto the inner shaft 22 as described above. The distal constraining member 146 may also include the distal retaining wire 188 that cooperatively engages a portion of the first loop 182 to releasably hold the first loop 182 on the stent 28 to allow the stent 28 to be expanded and collapsed repeatedly in cooperation with the proximal constraining member 144 for proper positioning within the patient's lumen. The distal retaining wire 188 may be proximally withdrawn from the first loop 182 to release the stent 28 from connection with the distal constraining member 146. The first loop 182 may be withdrawn with the device 10 from the patient and released from the stent 28. As will be understood by one skilled in the art, the proximal constraining member 144 may be connected to the inner shaft 22 and the distal constraining member 146 may be connected to the outer shaft 24 and be movable in equal and opposite directions by operation of the proximal portion 58 of the handle 26.

Figure 6E:
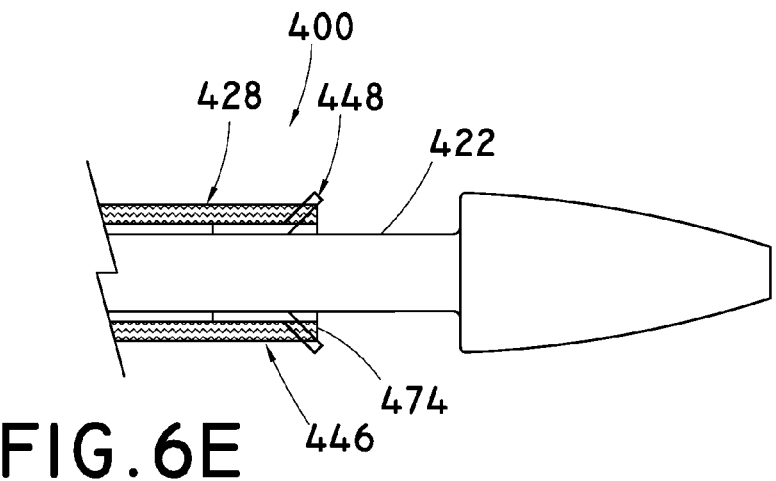
FIG. 6E is a partial side view of an alternative embodiment of a distal constraining member.
Figure 6F:
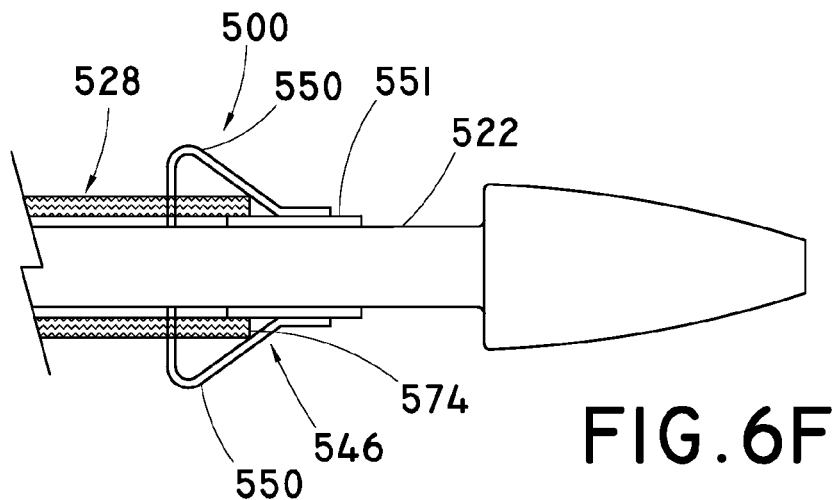
FIG. 6F is a partial side view of an alternative embodiment of a distal constraining member.

FIGS. 6E and 6F illustrate alternative embodiments of a distal constraining member 446, 546. A similar proximal constraining member is also provided, but not shown. The distal constraining member 446 shown in FIG. 6E includes one or more hooks 448 that may hook onto peaks 474 of the stent 428 to constrain the stent on an inner shaft 422. A plurality of hooks 448 may be provided on the inner shaft 422 and spaced apart to evenly hold the stent 428 in position. For example, 4 hooks may be provided and spaced apart by 90°. Other combinations of numbers of hooks and spacing of the hooks may also be provided, including uneven spacing and uneven numbers of hooks. One or more hooks 448 may be provided with a retaining wire 488 (not shown) extending through the hook 448 and the stent peak 474 to releasably lock the stent 428 to the delivery system 400, for example, similar to the embodiment described above with reference to FIGS. 6A-6C.

The distal constraining member 446 may also include a loop 482 (not shown) similar to the loop 82 described above that is woven between the peaks 474 and the hook 448 connects to the loop 482 to constrain the stent 428. The hook 448 may be released from the stent peak 474 or the loop 482 by advancing the proximal and distal constraining members 444, 446 towards each other reducing the tension of the stent 428 and releasing the hook 448. The hook 448 may also be released by withdrawing the retaining wire 488 and releasing the lock between the peak 474 and the hook 448, for example. The stent 428 may be expanded and constrained a plurality of times prior to release of the retaining wire 488 similar to the embodiments described above.

FIG. 6F illustrates the distal constraining member 546 that includes one or more grasping members 550 that grasp a portion of a stent 528 to constrain the stent on an inner shaft 522. The grasping members 550 may be provided on the inner shaft 522 and spaced apart to hold the stent 528 in position similar to the arrangements described above for the hooks 428. One or more grasping members 550 may be provided with a retaining wire 588 (not shown) extending through the grasping member 550 and the stent 528 to releasably lock the stent 528 to the delivery system 500 similar to the embodiments described above. The distal constraining member 546 may also include a loop 582 (not shown) similar to the loop 82 described above that is woven between the peaks 574 of the stent 528 and the grasping member 550 connects to the loop 582 to constrain the stent 528. The grasping member 550 may be released from the stent 528 or the loop 582 by opening the grasping member 550 away from the stent 528, for example by pressing on a distal portion 551 of the grasping member 550 to flex the grasping member 550 open. The stent 528 may be expanded and constrained a plurality of times prior to release of the retaining wire 588 similar to the embodiments described above.

Figure 6G:
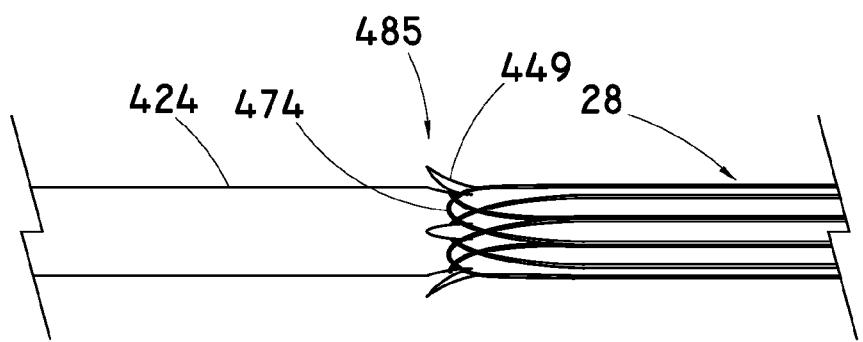
FIG. 6G is a partial side view of an alternative embodiment of a proximal constraining member.
Figure 6H:
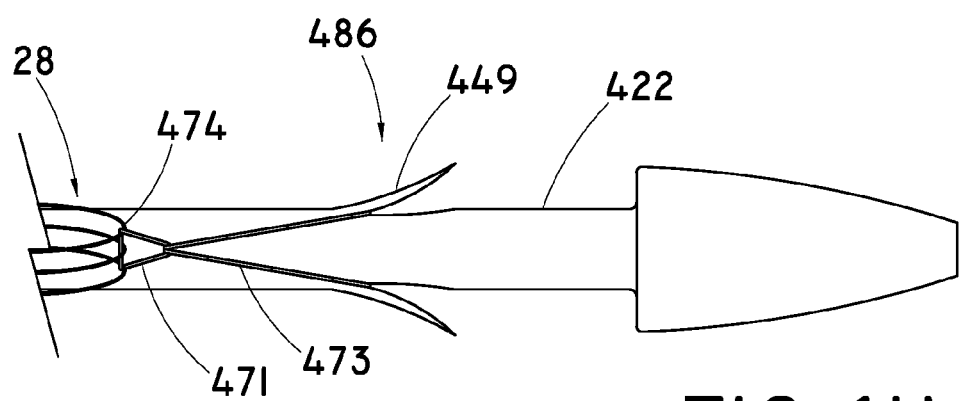
FIG. 6H is a partial side view of a distal constraining member.

FIGS. 6G and 6H illustrate an alternative embodiment of proximal and distal constraining members 485, 486 where the proximal constraining member 485 is different from the distal constraining member 486. In the embodiment shown in FIGS. 6G and 6H, the proximal and distal constraining members 485, 486 cooperatively apply and release tensioning force on the stent 28. The proximal constraining member 485 shown in FIG. 6G includes one or more hooks 449 that have been skived from the outer catheter 424 and that peaks 474 of the stent 28 hook over to constrain the stent 28 on the inner shaft 422. The skived hooks 449 may be positioned around the outer catheter 424 at a plurality of positions to hold the stent 28 against the inner catheter 422.

As shown in FIG. 6H, the distal constraining member 486 includes one or more hooks 449 that have been skived from the inner catheter 422. The distal constraining member 486 may also include a first loop 471 that is woven through one or more peaks 474 of the stent 28. The distal constraining member 486 may also include a second loop 473 that is woven through the first loop 471 and draws the first loop peaks 471 together and collapses the peaks 474 of the stent 28 against the inner catheter 422. The second loop 473 may be connected to the one or more hooks 449 on the inner catheter 422. Similar to the embodiments described above, the proximal and distal constraining members 485, 486 allow the stent 28 to be repeatedly expanded and contracted for proper positioning within the patient. The proximal and distal constraining members 485, 486 described and shown in FIGS. 6G and 6H may also be reversed so that the configuration of the distal constraining member 486 is connected to the proximal portion of the stent 28 and the configuration of the proximal constraining member 485 is connected to the distal portion of the stent.

Figure 7A:
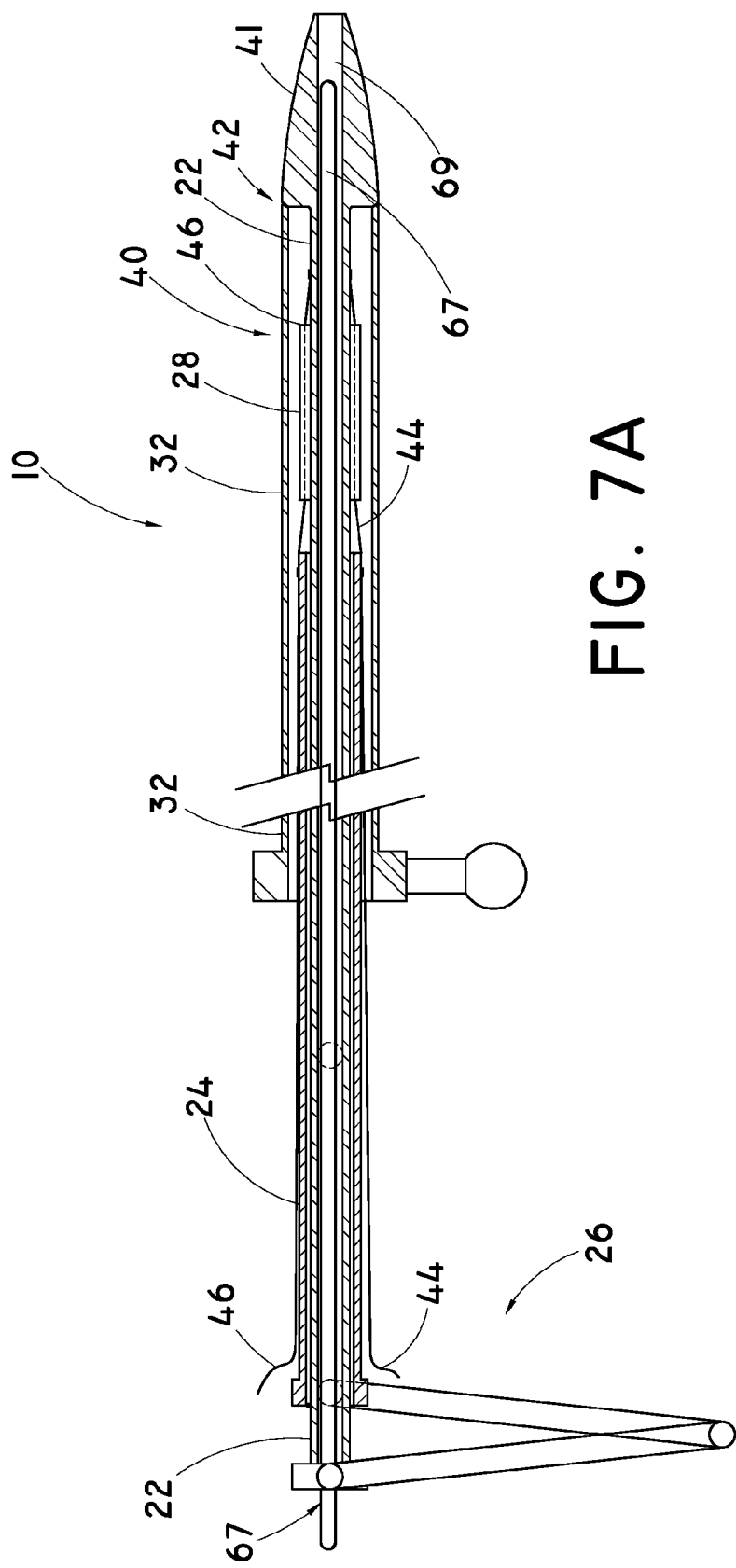
FIGS. 7A and 7B are sectional views of a delivery system illustrating a stiffening member.
Figure 7B:
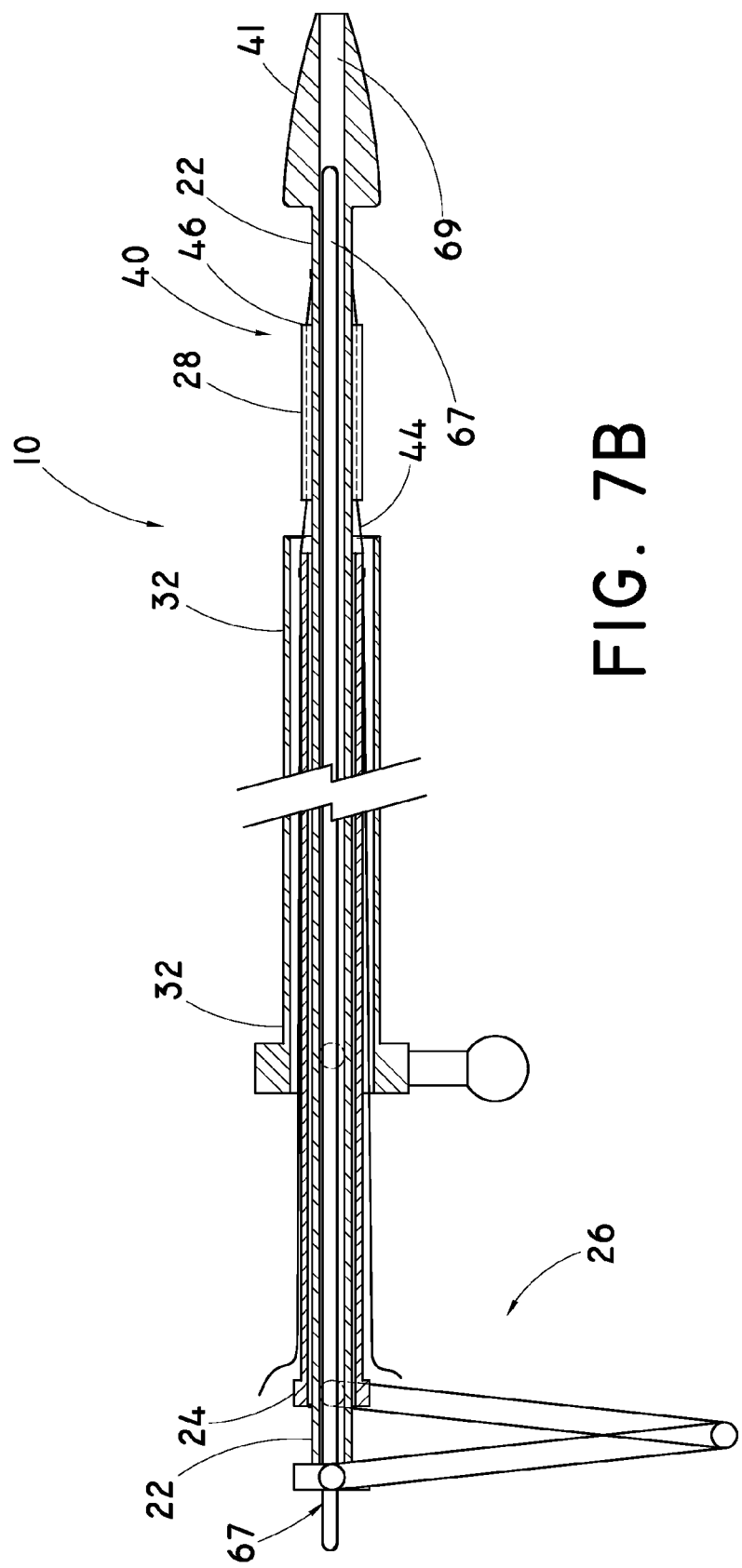

In some embodiments, a stiffening member 67 may be removably provided in a lumen 69 of the inner shaft 22 as shown in FIGS. 7A and 7B. The stiffening member may be provided as a mandril, catheter, rod and the like that is removably insertable into the lumen 69. The stiffening member 67 may be provided to help increase the rigidity of the inner catheters 22 against the inward tensioning force of the stent 28 when the stent 28 is in the constrained configuration 40. In some embodiments, the inner shaft 22 may be provided in a soft material to facilitate passage through the body lumen. In the event that the materials are sufficiently soft, the inner catheter 22 may collapse or deform in response to the tensioning force of the stent 28 provided by the first and second constraining members 44, 46 longitudinally constraining the stent 28 against the inner shaft 22. The stiffening member 67 may be made from any material having suitable stiffness to provide support for the inner shaft 22 with the stent 28 longitudinally tensioned on the inner shaft 22. Exemplary materials for forming the shaft include, but are not limited to, metal alloys such as stainless steel, tantalum or its alloys, tungsten, platinum, gold, copper, palladium, rhodium, or a superelastic alloys, such as nitinol or polymers that can be provided with sufficient shore hardness, such as Pebax, Peek, polyimide, liquid crystal polymers (LCP) such as Vectran, polyethylene, polyethylene terephthalate and Nylon. As shown in FIG. 7A, the outer sheath 32 may be provided for delivery of the stent to the area of the treatment site. The outer sheath 32 compresses the stent against the inner shaft 22 for delivery of the device 10 to the treatment site with the stiffening member 67 removed and the stent 28 in the constrained configuration 40. (See FIG. 1.) The stiffening member 67 may be inserted into the lumen 69 when the stent 28 is near the proper position for implantation into the patient and the outer sheath is over the stent 28 as shown in FIG. 7A. The outer sheath 32 may be withdrawn and the stent 28 remains constrained on the inner shaft 22 by the proximal and distal constraining members 44, 46. The stiffening member 67 supports the inner shaft 22 against the compressive tensioning force exerted by the proximal and distal constraining members 44, 46.

FIG. 8 illustrates a sectional view of the distal portion 31 of the stent delivery device 10 provided in a rapid exchange configuration. FIGS. 9A-9D show cross sectional views of an exemplary lumen configuration through the device 10 along different portions indicated in FIG. 8 in relation to a working channel of an endoscope. Many other lumen configurations are possible with the stent delivery device 10 and the following discussion is provided by way of non-limiting example. A working channel 100 of an endoscope is represented by the dashed line in FIGS. 9A-9D. FIG. 9A shows the cross sectional view along line A-A of FIG. 8 that is distal to the stent 28. The cross section view in FIG. 9A illustrates an inner catheter 110 having a first lumen 112 and a second lumen 114. A guide wire 118 is shown in the first lumen 112 and a first retaining wire 120 is shown in the second lumen 114. The first retaining wire 120 is a component of the distal constraining member 46. FIG. 9B shows the cross sectional view along line B-B of FIG. 8 taken proximal to the stent 28 and shows the inner shaft 110 within a first lumen 132 of an outer shaft 130 in relation to the working channel 100. A second retaining wire 134 is shown within a second lumen 136 of the outer shaft 130. The second retaining wire 134 is a component of the proximal constraining member 44 shown in FIG. 8.

FIG. 9C illustrates the cross sectional view taken along line C-C of FIG. 8. FIG. 9C illustrates a rapid exchange port 140 within a distal portion 31 of the device 10. The rapid exchange port 140 provides access to the first lumen 132 of the outer shaft 130 and to the first lumen 112 of the inner shaft 110. As shown in FIG. 9C, the guide wire 118 is being exchanged in the rapid exchange port 140.

FIG. 9D illustrates the cross sectional view taken along line D-D in FIG. 8 proximal to the rapid exchange port 140. FIG. 8D illustrates the wire guide 118, or other device suitable for insertion into the rapid exchange port 140, external to the outer shaft 130 and within the working channel 100 of the endoscope. The inner shaft 110 is enclosed within the first lumen 132 of the outer catheter 130.

The stent delivery system 10 may also be provided in an over-the-wire configuration, for example, as shown in FIG. 1. In the over-the-wire configuration, the first lumen 112 of the inner shaft 110 is accessible from the proximal end portion of the inner shaft 110. In the over-the-wire configuration, the cross sectional views taken along the lines C-C and D-D would be the same as the cross-sectional view taken along line B-B as shown in FIG. 9B.

Figure 10A:
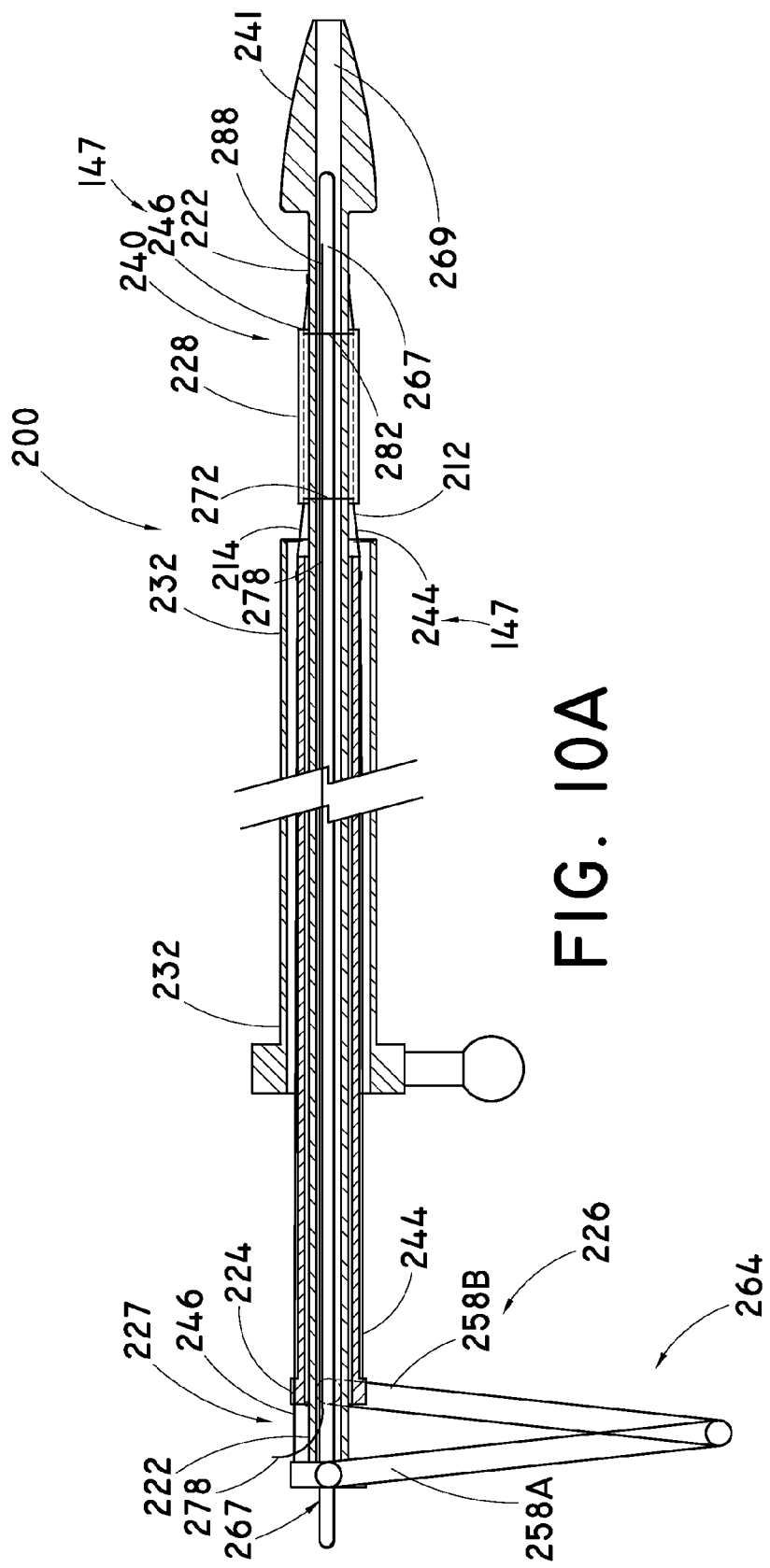
FIGS. 10A and 10B are side views of a delivery system having alternative constraining members.
Figure 10B:
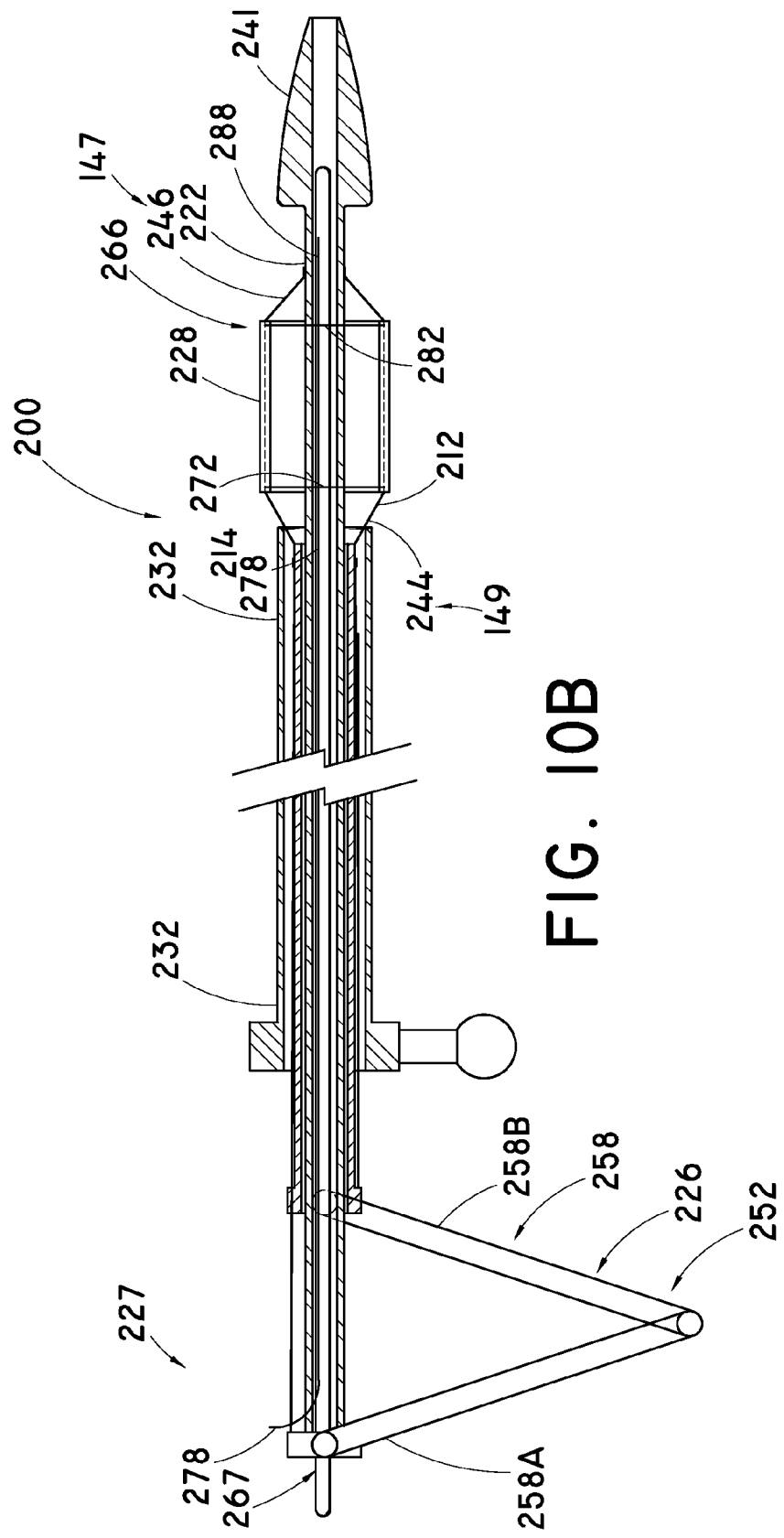

As shown in FIGS. 10A and 10B, a stent delivery system 200 may be provided with two wires 212, 214 to control the expansion and contraction of a stent 228. The stent delivery system 200 includes an inner shaft 222 and a handle 226 at a proximal portion 227 of the system 200. The stent 228 is positionable on the inner shaft 222 at a distal portion 231 of the stent delivery system 200. The stent delivery system 200 may optionally include an outer sheath 232 slidably positionable over a portion of the inner shaft 222 to cover the stent 228. The stent delivery system 200 may also include an optional stiffening member 267 similar to the stiffening member 67 described above with reference to FIGS. 7A and 7B. The stent 228 is shown in FIG. 10A in a constrained configuration 240. Similar to the stent 28 described above, the stent 228 is movable between the constrained configuration 240 and an expanded configuration 266 shown in FIG. 10B. The stent 228 is moved between the constrained and expanded configuration with a proximal constraining member 244 and a distal constraining member 246.

The proximal and distal constraining members 244, 246 cooperatively apply and release longitudinal tension on the stent 228 to move the stent between the constrained configuration 240 and the expanded configuration 266. In the embodiment shown in FIGS. 10A and 10B, the wires 212 and 214 of the proximal and distal constraining members 244, 246, respectively move in equal and opposite directions in connection with arms 258a, 258b of the handle portion 258 moving in equal and opposite directions. By way of non-limiting example, the handle 226 is shown in an open position 264 that holds the proximal and distal constraining members 244, 246 apart in a first position 147 to apply longitudinal force to the stent 228 to hold the stent 228 against the inner shaft 222 in the constrained configuration 240 as shown in FIG. 10A. In FIG. 10B, the arms 258a, 258b are moved to a closed position 252 and the proximal and distal constraining members 244, 246 are moved closer together in a second position 149 and release the tension on the stent 228 so the stent 228 moves to an expanded configuration 226 with the proximal and distal constraining members 244, 246 still connected to the stent 228. Similar to the embodiments described above, the stent 228 may be moved between the expanded and constrained configurations 266, 240 multiple times until the correct position within the patent's lumen is obtained.

The proximal constraining member 244 may include the wire 212, a loop 272 and a proximal retaining wire 278. The wire 212 may be provided with a loop to overlap with the loop 272 so that the proximal retaining wire 278 may releasably lock the wire 212 and the loop 272 together until the proximal retaining wire 278 is withdrawn. The distal constraining member 246 may be provided with the wire 214, a loop 282 and a distal retaining wire 288 in a similar arrangement to the proximal constraining member 244. The proximal and distal retaining wires 278, 288 may be proximally withdrawn to completely release the stent 228 when the stent 228 is properly positioned.

FIG. 11 illustrates a stent delivery system 300 in accordance with another embodiment of the present invention. The stent delivery system 300 includes an inner shaft 322, an outer shaft 324 (see FIG. 12) and a handle 326 at a proximal portion 327 of the system 300. A stent 328 (shown in FIG. 12) is positionable on a stent region 330 of the inner shaft 322 at a distal portion 331 of the delivery system 300. The stent delivery system 300 may optionally include an outer proximal sheath 332 and an outer distal sheath 333 slidably positionable over a portion of the inner shaft 322 to cover the stent 328. The proximal outer sheath 332 may be proximally withdrawn and the distal outer sheath 333 may be separately and distally withdrawn to expose the stent 328. A guide wire 336 may be extendable through a port 338 of the inner shaft 322 to a distal tip 341 at the distal portion 331 of the stent delivery system 300. An optional stiffening member 367 may be insertable into the inner shaft 322 similar to the stiffening member 67 described above with reference to FIGS. 7A and 7B.

FIG. 12 illustrates a sectional view of the stent delivery system 300. As shown in FIG. 12, the stent 328 is in a constrained configuration 340 collapsed against the inner shaft 322. The optional proximal outer sheath 332 is shown extended over a proximal portion 329 of the stent 328. The distal outer sheath 333 is shown extended over a distal portion 335 of the stent 328. The stent 328 is held in the constrained configuration by a proximal constraining member 344 and a distal constraining member 346 that provide a longitudinal tensioning force to hold the stent 328 in the constrained configuration 340. When present, the outer sheath 322 may provide some compressive force to the stent 328 in addition to the proximal and distal constraining members 344, 346. Alternatively or additionally, the distal portion 335 of the stent 328 may be constrained by the distal outer sheath 333. The proximal and distal constraining members 344, 346 are operably connected to the handle 326. A lock 353 may be provided to releasably lock the handle 326 in a closed position 352 shown in FIG. 11. The handle 326 may include a sheath lock 337 to releasably hold the proximal outer sheath 332 in the proximally withdrawn position shown in FIG. 13.

As shown in FIG. 13, the proximal outer sheath 332 has been proximally withdrawn exposing the proximal portion 329 of the stent 328 and the outer sheath 332 may be locked to the handle 326 using the sheath lock 337. The stent 328 is held in the constrained configuration 340 by the proximal constraining member 344, the distal constraining member 346. The distal outer sheath 333 is positioned over the distal portion 335 of the stent 328. The handle 326 is in the closed position 352. Arms 358a, 358b of the handle 326 are operatively connected to the inner shaft 322 and the outer shaft 324 to move the inner and outer shafts 322, 324 relative to each other.

FIG. 14 illustrates the stent 328 with the proximal portion 329 of the stent 328 in an expanded configuration 368. The distal portion 335 of the stent 328 is covered by the distal outer sheath 333 and remains constrained. As shown in FIG. 14, the stent 328 may be expanded at the proximal portion 329 for proper placement of the proximal portion 329 within the patient's lumen and then the distal portion 335 of the stent 328 may be expanded by the distal withdrawal of the outer distal sheath 333 to allow the distal portion 335 to expand. Both the proximal and distal constraining members 344, 346 remain connected to the stent 328 in the expanded configuration 368 to allow the stent 328 to be repositioned between the expanded and constrained configurations 340, 368 until the stent 328 is optimally positioned within the patient's lumen.

As shown in FIG. 14, the arms 358a, 358b have been moved to the open position 364 of the handle 326 which in turn moves the inner and outer shafts 322, 324 relative to each other to release the longitudinal tension of the proximal and distal constraining members 344, 346 from the stent 328. Similar to the delivery systems described above, the stent 328 may be completely released from the proximal and distal constraining members 344, 346 by removal of restraining members 378, 388 that are part of the proximal and distal constraining members 344, 346.

FIGS. 15-18 illustrate an embodiment of a stent delivery system 600. The delivery system includes an inner shaft 622 and an outer shaft 624. As shown in FIG. 15, a stent 628 is in a constrained configuration 640 collapsed against the inner shaft 622. A proximal outer sheath 632 is shown extended over a proximal portion 629 of the stent 628. A distal outer sheath 633 is shown extended over a distal portion 635 of the stent 628. Proximal and distal constraining members 644, 646 are also provided. The proximal and distal constraining members may cooperatively work together with the proximal and distal outer sheaths 632, 633 to longitudinally tension the stent 628 in the constrained configuration 640 with the proximal and distal constraining members 644, 646 in a first position 647. A handle 626 is connected to a proximal portion 627 of the delivery system 600 and includes arms 658a, 658b and is shown in a closed position 652. The proximal and distal constraining members 644, 646 are operably connected to the handle 626. The proximal sheath 632 and the distal sheath 633 are also operably connected to the handle 626.

As shown in FIG. 16, the proximal outer sheath 632 has been proximally withdrawn to a first withdrawn position 641 to expose a central portion 643 of the stent 628 but still covers the proximal portion 629 of the stent 628. The distal outer sheath 633 is positioned over the distal portion 635 of the stent 628. The handle 626 is in a closed position 652. The stent 628 remains in the constrained configuration 640 by the proximal and distal constraining members 644, 646 with the proximal outer sheath 631 in the first withdrawn position 641. The proximal and distal constraining members 644, 646 may each optionally include a retaining wire (not shown).

FIG. 17 illustrates the stent 628 of the delivery system 600 with the central portion 643 of the stent 628 in an expanded configuration 667. The handle 626 is shown an open position 664 with arms 658a, 658b spaced apart. The opening of the arms 658a, 658b operatively moves the proximal and distal constraining members 644, 646 closer together to a second position 649 and the central portion 643 of the stent 628 is moved to the expanded configuration 667. The operator may control the speed and force with which the handle 626 is opened that in turn operatively controls speed and extent of the expansion of the central portion 643 of the stent 628 to facilitate proper placement of the stent 628 within the patient's lumen. As shown in FIG. 17, the proximal outer sheath 632 and the distal outer sheath 633 cover the proximal portion 629 and the distal portion 635 of the stent 628 and the proximal and distal constraining members 644, 646, respectively. The stent 626 may be recollapsed to the constrained configuration 640 shown in FIG. 16 by moving the handle 626 to the closed position 652 and returning the proximal and distal constraining members 644, 646 to the first position 647 by moving the inner and outer shafts 622, 624 relative to each other. The delivery system 600 may also be used as a mechanical stricture dilator. Applying additional opening force to the arms 658a, 658b of the handle 626 supplies additional radial expansion force, above the self-expanding forces of a self-expanding stent, to the stricture as the stent 628 is expanded against the stricture. The additional radial expansion force acts to increase the dilation effect of the stent 628 against the stricture.

FIG. 18 illustrates the stent 628 of the stent delivery system 600 in an expanded configuration 669. As shown, the proximal outer sheath 632 has been proximally withdrawn to expose the proximal portion 629 of the stent 628. The distal outer sheath 633 has been distally withdrawn to expose the distal portion 635 of the stent 628 and allow complete expansion of the stent 628 for implantation into the patient's lumen. If proximal and distal retaining wires are included, the retaining wires may be withdrawn before, after or at the same time the proximal and distal outer sheaths 632, 633 are withdrawn.

FIGS. 19A-19G illustrate alternative embodiments of a distal constraining member 646a-646e that operates similarly to the distal constraining member 646 described above to move the stent 628 between the constrained configuration 640 and the expanded configuration 667, 669. A similar proximal constraining member is also provided for each of the embodiments of the distal constraining members 646a-646e, but not shown, and may be connected to the outer shaft and cooperatively work with the distal constraining member 646a-646e. Only reference to the distal portion will be made. The distal constraining member 646a shown in FIG. 19A includes a high friction surface 650 on the inner shaft 622. By way of non-limiting example, the high friction surface 650 may be a material with a high coefficient of friction or a coating of a releasable adhesive. The high friction surface 650 is positioned between the inner shaft 622 and the distal outer sheath 633 so that the distal portion 635 of the stent 628 is releasably locked to the inner shaft 622. With the distal outer sheath 633 positioned over the distal portion 635 of the stent 628, the stent 628 may be moved between the expanded configuration 667 and the constrained configuration 640 as shown in FIGS. 16 and 17. The stent 628 may be released from the inner shaft 622 by distally withdrawing the distal outer sheath 633 so that the distal end 635 of the stent 628 is exposed and expanded.

An alternative embodiment of the distal constraining member 646b shown in FIGS. 19B-19D includes a mechanical fixing member 660 on the inner shaft 622. By way of non-limiting example, the mechanical fixing member 660 may include a tube 662 with at least one tab 664. Wires of the stent 628 at the distal portion 635 are releasably held in position over the tabs 664 and the distal outer sheath 633 is shown positioned over the distal portion 635 of the stent 628. A cross section of the mechanical fixing member 660 is shown in FIG. 19B and a longitudinal section of the mechanical fixing member 660 is shown in FIG. 19C. Other shapes and patterns of tabs 664 may also be used. The tube 662 may be crimped or glued to the inner shaft 622 or the tabs 664 may be connected to the inner shaft 622 by other means known to one skilled in the art. The distal portion 635 of the stent 628 may automatically disengage from the tabs 664 when the distal outer sheath 633 is distally withdrawn from the stent 628 to release the stent to the expanded configuration 669.

An alternative embodiment of the distal constraining member 646c shown in FIG. 19E and includes a sleeve member 670 on the inner shaft 622. The sleeve member 670 may be made of a high friction material similar to the high friction surface 650. The sleeve member 670 is positioned between the stent 628 and the distal outer sheath 633 so that the distal portion 635 of the stent 628 is releasably locked to the inner shaft 622. The stent 628 may be released from the inner shaft 622 by distally withdrawing the distal outer sheath 633 and the sleeve member 670 so that the distal end 635 of the stent 628 is exposed and the stent 628 expanded to the expanded configuration 669.

An alternative embodiment of the distal constraining member 646d shown in FIG. 19F. The distal constraining member 646d includes at least one bead 680, each bead 680 connected to a line 682. The line 682 is connected to the inner shaft 622 and extents through a loop of the stent 628 at the distal portion 635. The inner shaft 622 includes a receptacle 684 sized and shaped to receive the bead 680 and allow the outer distal sheath 633 to slide over the distal portion 635 of the stent 628. The bead 680 positioned in the receptacle 680 and the distal outer sheath 633 over the bead 680 to releasably hold the stent 628 in the constrained configuration 640. The stent 628 may be released from the inner shaft 622 by distally withdrawing the distal outer sheath 633 and releasing the bead 680 from the receptacle 680 so that the stent 628 is released and the bead 680 connected to the line 682 is withdrawn through the loop of the stent 628 and remains with the inner shaft 622 with the stent 628 in the expanded configuration 640.

An alternative embodiment of the distal constraining member 646e shown in FIG. 19g and includes a retaining wire 688 extending through a loop of the stent 628 in the distal portion 635. The distal outer sheath 633 is positioned over the retaining wire 688 through the stent loop so that the distal portion 635 of the stent 628 is releasably locked to the inner shaft 622. The stent 628 may be released from the inner shaft 622 by distally withdrawing the distal outer sheath 633 and proximally withdrawing the retaining wire 688. The distal end 635 of the stent 628 is exposed and released and the stent 628 expands to the expanded configuration 669.

Figure 20:
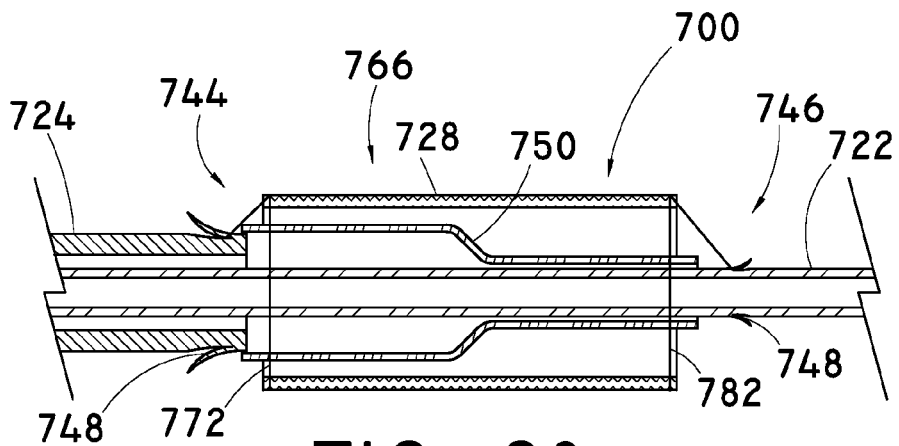
FIG. 20 is a partial sectional view of a stent delivery system including a release member.
Figure 21:
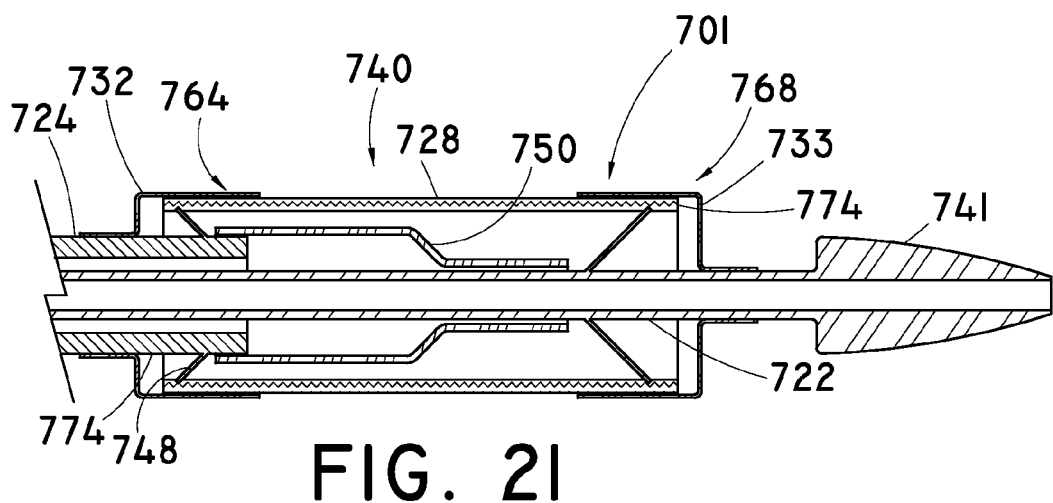
FIG. 21 is a partial sectional view of an alternative embodiment of a stent delivery system including a release member.
Figure 22:
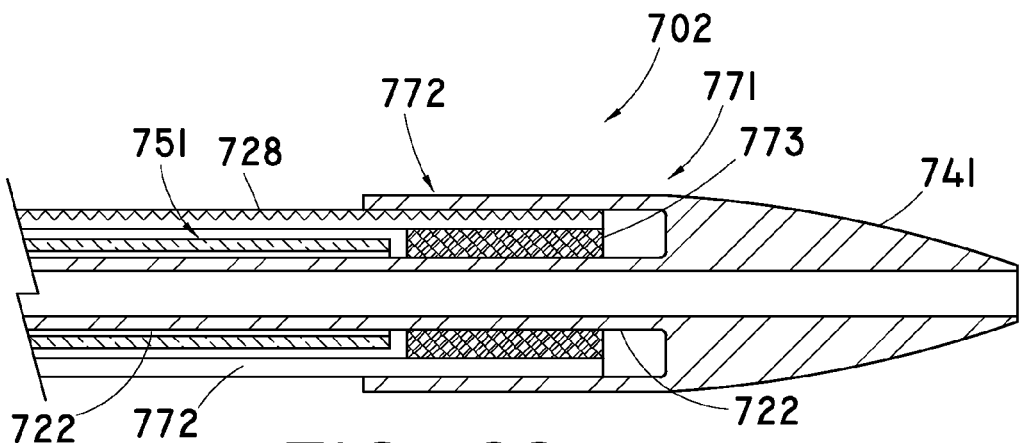
FIG. 22 is a partial sectional view of an alternative embodiment of a stent delivery system including a release member.

As shown in FIGS. 20-22, a release member may also be included with a stent delivery system 700. As shown in FIG. 20, the stent delivery system 700 includes an inner catheter 722, an outer catheter 724 and a stent 728. The delivery system 700 also includes proximal and distal constraining members 744, 746. As shown in FIG. 20, the proximal constraining member 744 includes hooks 748 on the outer catheter 724 and a loop 772 woven through the stent 728. The distal constraining member 746 includes hooks 748 on the inner catheter and a loop 782 woven through the stent 728. The proximal and distal constraining members 744, 746 releasably hold the stent 728 to the inner catheter 722 and to allow repeated expansion and compression of the stent 728. The stent 728 is shown in the expanded configuration 766 in FIG. 20.

The stent delivery system 700 also includes a release member 750 positioned between the inner catheter 722 and the stent 728. The release member 750 may be provided as a tubular member that is free floating over the inner catheter 722. The system 700 is shown with the inner and outer catheters 722, 724 pushed inward towards each other so that the constraining members 744, 746 are positioned closer together to release the tension on the stent 728 and allow the stent 728 to expand to the expanded configuration 766. Once the stent is properly positioned within the patient, the loops 772, 782 may be completely released from the hooks 748 by further pushing the proximal and distal constraining members 744, 746 closer together so that the release member 750 contacts the hooks 748 on both the proximal and distal portions and releases the loops 772, 778 from the hooks 748 and releasing the stent 728 completely from the delivery system 700. A handle (not shown) may include stops or indicators to indicate an expansion position for the constraining members 744, 746 and a complete release position for the constraining members 744, 746.

FIG. 21 illustrates a delivery system 701 including the release member 750 in an embodiment that does not include a proximal or distal loop as part of proximal and distal constraining members 764, 768. As shown in FIG. 21, the delivery system 701 includes the inner catheter 722, the outer catheter 724, the stent 728 and proximal and distal constraining members 764, 768 connected to the outer catheter 724 and the inner catheter 722, respectively. The delivery system 701 as shown also includes proximal and distal outer sheaths 732, 733, respectively, that compress the stent 728 against the inner catheter 722 in a compressed configuration 740 shown in FIG. 21. The proximal and distal outer sheaths 732, 733 may include a friction fit portion or a spring at the proximal and distal ends to keep the stent 728 constrained against the inner catheter, for example, during insertion of the delivery system 710 through an endoscope or a bodily lumen. The release member 750 is positioned between the inner catheter 722 and the stent 728 and may be freely movable.

The proximal and distal constraining members 764, 768 include one or more hooks 748 that hook through peaks 774 of the stent 728 to hold the stent 728 to the inner catheter 722. As described above, the stent 728 may be expanded to an expanded configuration 766, by moving the proximal and distal constraining members 764, 768 inward while the outer sheaths 732, 733 are positioned over the ends of the stent 728 to allow reconstraining of the stent 728 until the stent 728 is properly positioned within the patient. With the stent 728 properly positioned within the patient, the proximal and distal constraining members 764, 768 are moved further inward toward each other and the release member 750 presses against the hooks 748 to release the hooks 748 from the stent 728. The proximal and distal outer sheaths 732, 733 are also displaced from the stent by contact with the release member 750 as the proximal and distal constraining members 764, 768 move closer together and the stent 728 is fully expanded.

Another embodiment of a stent delivery system 702 is shown in FIG. 22. The stent delivery system 702 includes the inner catheter 722, the stent 728 and a release catheter 751. The distal constraining member 771 is shown and includes a distal outer sheath 772 connected to a distal tip 741 and a circular member 773 surrounding the inner catheter and positioned between the inner catheter and the stent 728. The stent 728 is positioned between the circular member 773 and the distal outer sheath 772. The friction between the stent 728 and the sheath 772 is higher than the friction between the stent 728 and the circular member 773. The release member 750 may be provided as a catheter, surrounding the inner catheter 722. The release member 750 may be pushed distally to release the stent 728 from the distal constraining member 771.

In some embodiments, a stent delivery system may be provided where a stent is delivered in a pre-tensioned configuration and the stent is not re-sheathable or re-collapsible as shown in FIGS. 23 and 24. A stent delivery system 800 is shown in FIG. 23 and includes an inner catheter 822 and a stent 828 mounted thereon and an outer sheath 832. The stent 828 is provided in a tensioned, constrained configuration 840 using proximal and distal constraining members 844, 846. As shown in FIG. 23, the proximal constraining member 844 includes a high friction surface 845 that may be provided on the inner catheter 822 between the inner catheter 822 and the stent 828. The distal constraining member 846 includes at least one hook 847 that extends through a loop 874 of the stent 828 to hold the stent 828 constrained to the inner catheter 822 in combination with the proximal constraining member 844. The outer sheath 832 is slidable over the stent 828 and may cover the stent 828 during delivery to the patient location. For release of the stent 828 into an expanded configuration (not shown), the outer sheath may be proximally withdrawn and the distal constraining member 846 exposed followed by the proximal constraining member 844. Once the proximal constraining member is released by the outer sheath 832, the stent 828 expands and is released by both the proximal and distal constraining members 844, 846 with the longitudinal tensioning force removed. One skilled in the art will recognize that the embodiments of the proximal and distal constraining members 844, 846 may also be reversed so that the high friction surface 845 is provided with the distal constraining member 846 and at least one hook 847 is provided with the proximal constraining member 844. The outer sheath 832 may be distally withdrawn to release the longitudinal tension on the stent 828. Any type of proximal and distal constraining members may be provided with the stent delivery system 801 that provide longitudinal tension to the stent 828 to hold the stent 828 constrained to the inner catheter 822 for delivery to the patient site. For example, the constraining members shown in FIGS. 19A-19G and described above may be provided with the stent delivery system 800.

A stent delivery system 801 is shown in FIG. 24 and includes an inner catheter 822 and a stent 828 positioned on the inner catheter 822 in a constrained configuration 840. The stent delivery system 801 also includes a proximal and distal constraining member 854, 856. Both the proximal and distal constraining 854, 856 members include at least one hook 847 that extends through a loop 874 of the stent 828 to hold the stent 828 longitudinally tensioned against the inner catheter 822. The hooks 859 may be skived from the inner catheter 822. A plurality of hooks 859 may be provided and spaced apart around the inner catheter 822 to help hold the stent 828 in the constrained configuration. The proximal constraining member 854 may further include a release line 862 connected to the hook 859 of the proximal constraining member. The release line 861 extends to the proximal portion of delivery system 801 and may be pulled proximally to release the hook 859 from the stent loop 874 from the proximal constraining member 844 and release the stent 828 from the constrained configuration 840. Similarly, the distal constraining member may include a distal release line 862 that extends to the proximal portion of delivery system 801 and may be pulled proximally to release the hook 859 from the stent loop 874 of the distal constraining member 856 and release the stent 828 from the constrained configuration 840. The stent delivery system 801 may further include a loop on the proximal constraining member 854, the distal constraining member 856 or both (not shown) that may be woven through the loops 874 of the stent 828 and then connected to the hook 859 similar to the loop described above with reference to FIGS. 5A-5C and 6H. The delivery system 801 may also include an outer sheath (not shown).

FIGS. 27A-27C illustrate a stent delivery system 1000 in accordance with embodiments of the present invention. The stent delivery system 1000 includes an inner shaft 1022, an outer shaft 1024 and a handle 1026 at a proximal portion 1027 of the system 1000. A stent 1028 is positionable on a stent region 1030 of the inner shaft 1022 at a distal portion 1031 of the delivery system 1000. The stent delivery system 1000 may optionally include an outer sheath slidably positionable over a portion of the outer shaft 1024 and the inner shaft 1022 to cover the stent region 1030 and the stent 1028 (See for example FIGS. 1 and 2). Similar to the embodiment shown in FIG. 1, the stent delivery system 1000 may also include one or more radiopaque markers and a guidewire extendable through a port 1038 of the inner shaft 1022 through a distal tip 1041 at the distal portion 1031 of the delivery system 1000.

FIG. 27A illustrates the stent delivery system 1000 with the stent 1028 in a constrained configuration 1040 collapsed against the inner shaft 1022. The stent 1028 may be a mechanically expandable stent that is crimped or otherwise positioned on the stent delivery system 1000 for delivery to a patient's lumen. The stent may be formed of any material known to one skilled in the art, for example, the stent may be formed from a metallic material such as nitinol or a plastic material. The stent delivery system 1000 may also include an expandable member 1025 that is operably connected to the inner shaft 1022 and the outer shaft 1024. The expandable member 1025 may be formed of a woven mesh, such as a double helical mesh. The mesh may be formed from any suitable material such as metal. In some embodiments, the expandable member 1025 may be formed of a polymeric materially that is expandable and has enough strength to also expand the stent 1028. The expandable member 1025 may be mechanically expanded by moving the inner and outer shafts 1022, 1024 relative to each other. For example, a first end portion 1029 of the expandable member 1025 may be operably connected to the outer shaft 1024 and a second end portion 1033 of the expandable member 1025 may be operably connected to the inner shaft 1022. The expandable member 1025 may be held on the inner and outer shafts 1022, 1024 using any technique known to one skilled in the art. The connection may be non-releasable for example by bonding welding gluing and the like, or releasable using constraining members similar to those described above. In some embodiments where the stent 1028 is mechanically expandable, the expandable member 1025 may be non-releasably connected to the inner and outer shafts 1022, 1024.

As shown in FIG. 27B, the expandable member 1025 may be radially expanded to expand the stent 1028 positioned thereon to an expanded configuration 1066. The expandable member 1025 may be expanded by moving the outer shaft 1024 distally and the inner shaft 1022 proximally so the end portions 1029, 1033 are moved towards each other and the expandable member 1025 expands axially. In some embodiments, the first end 1029 may be connected to the inner shaft 1022 and the second end 1033 may be connected to the outer shaft 1024 so that the expansion of the expandable member 1025 occurs when the inner shaft 1022 is moved distally and the outer shaft 1024 is moved proximally. In some embodiments, the expandable member 1025 may be formed of a woven mesh such as a double helical mesh. The amount and speed of the expansion of the expandable member 1025 may be controlled by movement of the handle 1026. In some embodiments, the inner and outer shafts 1022, 1024 may be moved in equal and opposite directions so that a midpoint 1035 of the stent 1028 remains in the same position when the stent 1028 is radially expanded by the expandable member 1025. In some embodiments, one of the inner or outer shafts 1022, 1024 may be moved to radially expand the stent 1028. The handle 1026 may include a lock as described above to releasably lock the handle 1026.

As shown in FIG. 27C, the stent 1028 is shown in the expanded configuration 1066 where the stent 1028 is expanded away from the inner shaft 1022 and represents the stent 1028 positioned in a lumen of the patient. The inner and outer shafts 1022, 1024 have been moved relative to each other so that the expandable member 1035 is collapsed against the inner shaft 1022 and the delivery system 1000 may be removed from the patient's lumen.

Figure 28A:
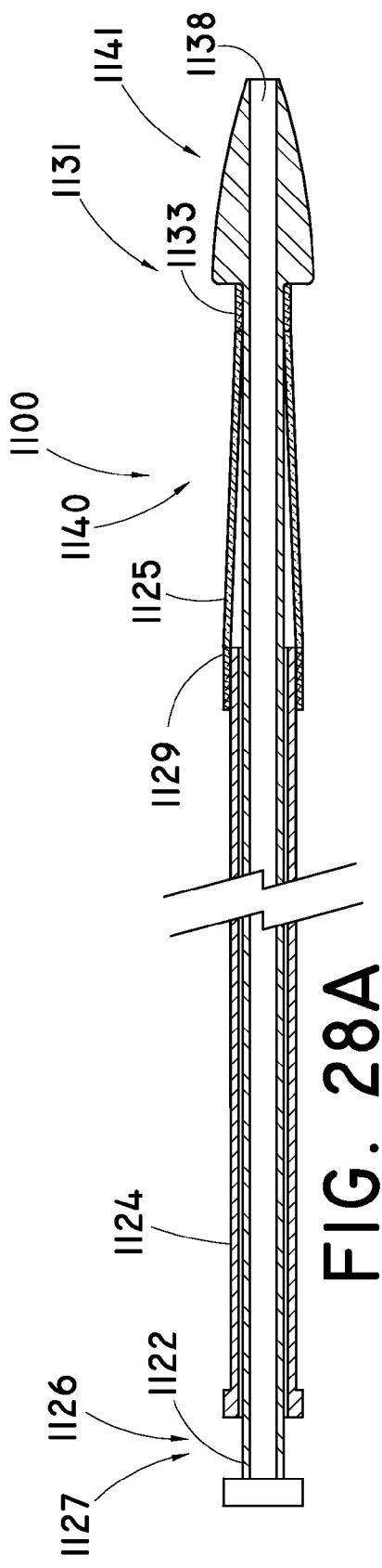
FIGS. 28A and 28B illustrate an embodiment of a dilator system.
Figure 28B:
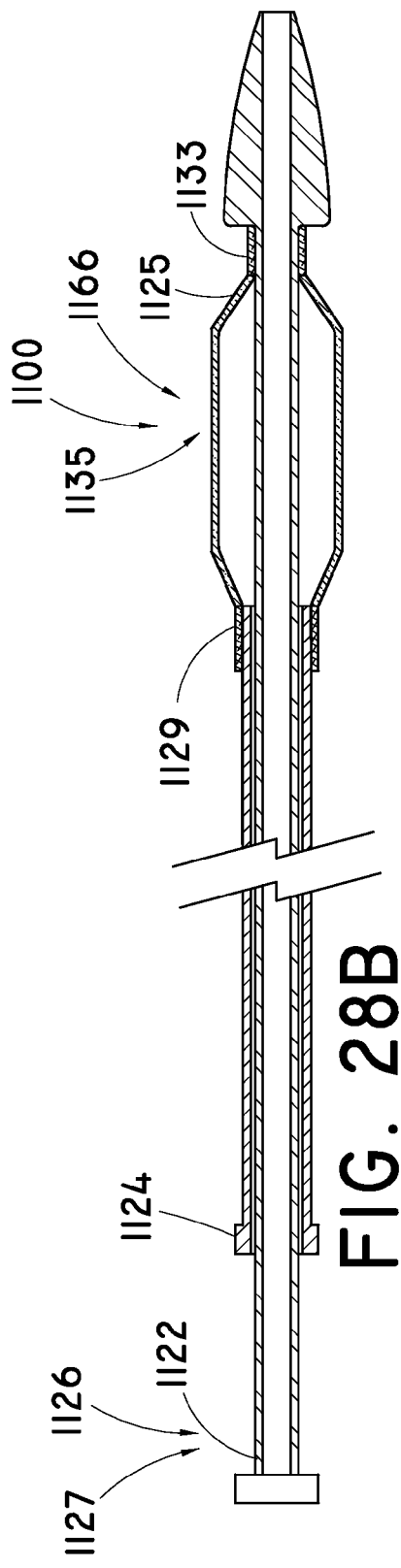

FIGS. 28A and 28B illustrate an embodiment of a mechanical dilator system 1100. The mechanical dilator system 1100 includes an inner shaft 1122, an outer shaft 1124 and a handle 1126 at a proximal portion 1127 of the system 1100. The dilator system 1100 may also include an expandable member 1125 that is operably connected to the inner shaft 1122 and the outer shaft 1124. The expandable member 1125 may be formed of a woven mesh, such as a double helical mesh. The mesh may be formed from any suitable material such as metal. In some embodiments, the expandable member 1125 may be formed of a polymeric materially that can be expanded in response to movement of the inner and outer shafts 1122, 1124. The dilator system 1100 may optionally include an outer sheath slidably positionable over a portion of the outer shaft 1124 and the inner shaft 1122 to cover the expandable member 1125 for delivery to the lumen position (See for example FIGS. 1 and 2). Similar to the embodiment shown in FIG. 1, the dilator system 1100 may also include one or more radiopaque markers and a guidewire extendable through a port 1138 of the inner shaft 1122 through a distal tip 1141 at a distal portion 1131 of the dilator system 1100.

As shown in FIG. 28A, the expandable member 1125 may be positioned in a collapsed configuration 1140 where the expandable member is collapsed against the inner shaft 1122, for example, for delivery through a patient's lumen such as a blood vessel or an airway. The expandable member 1125 may be mechanically expanded by moving the inner and outer shafts 1122, 1124 relative to each other. For example, a first end portion 1129 of the expandable member 1125 may be operably connected to the outer shaft 1124 and a second end portion 1133 of the expandable member 1125 may be operably connected to the inner shaft 1122. The expandable member 1125 may be held on the inner and outer shafts 1122, 1124 using any technique known to one skilled in the art. The connection may be non-releasably connected, for example by bonding welding gluing and the like.

As shown in FIG. 28B, the expandable member 1125 may be radially expanded to an expanded configuration 1166. The expandable member 1125 may be expanded by moving the outer shaft 1124 distally and the inner shaft 1122 proximally so the end portions 1129, 1133 are moved towards each other and the expandable member 1125 expands axially. In some embodiments, the first end 1129 may be connected to the inner shaft 1122 and the second end 1133 may be connected to the outer shaft 1124 so that the expansion of the expandable member 1125 occurs when the inner shaft 1122 is moved distally and the outer shaft 1124 is moved proximally. The amount and speed of the expansion of the expandable member 1125 may be controlled by movement of the handle 1126. In some embodiments, the inner and outer shafts 1122, 1024 may be moved in equal and opposite directions so that a midpoint 1135 of the expandable member 1125 remains in the same position when the expandable member 1125 is radially expanded. In some embodiments, one of the inner or outer shafts 1122, 1124 may be moved to radially expand the expandable member 1125. The handle 1126 may include a lock as described above to releasably lock the handle 1126.

The mechanical dilator system 1100 may be used instead of a balloon dilator and advantageously may be readily collapsed against the inner shaft 1122 more quickly than deflating a balloon. Additionally, when the expandable member is formed from a mesh, blood and air may pass through the expandable member 1125 in the expanded configuration 1166 that is not possible with an expanded balloon. In some embodiments, the expandable member 1125 may also include wings or other protrusions that help to hold the expandable member 1125 in position within the lumen when the expandable member is in the expanded configuration 1166 and the dilator system 1100 is used as an anchoring device (not shown).

The materials used to manufacture the components of the stent delivery systems and mechanical dilator systems described herein may be any materials known to one skilled in the art that are suitable for use in patients. By way of non-limiting example, the shafts and sheaths may be formed from polytetrafluorothylene (PTFE) particularly when a low friction outer sheath is desirable. Nylon and HDPE may also be used for clarity. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon including multi-layer or single layer structures and the like and may also include reinforcement wires, braid wires, coils, coil springs and or filaments. The stent may be formed from but is not limited to the following materials: Nickel titanium alloys, for example, nitinol, stainless steel, cobalt alloys and titanium alloys. The loops of the constraining members may be made from common suture material as known in the art, for example polyester suture such as 4-0 Tevdek®, nylon, silk, polypropylene, ultra high molecular weight polyethylene (UHMPE) and the like. The sutures may be monofilament, braided, twisted or multifilament. The loops and the retaining wires may also be made from a metallic alloy such as stainless steel or nickel titanium. In some embodiments, the stent, the loops and/or the retaining wires may be made from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols poly-orthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, poly-glutamic acid, poly-lysine, gelatin, fibrin, fibrinogen, casein, collagen.

Figure 25A:
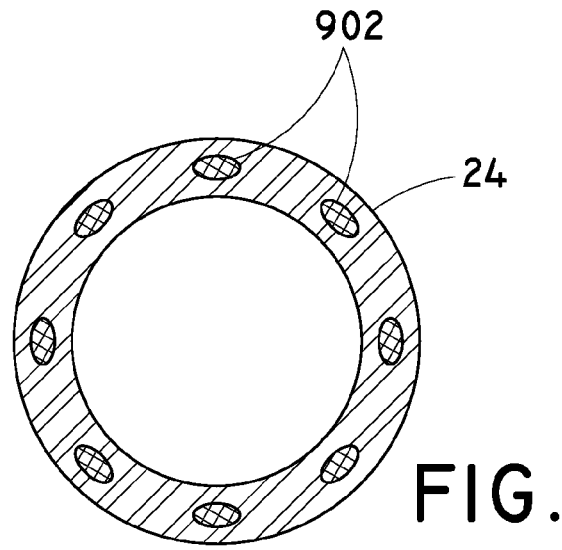
FIGS. 25A-25C illustrate cross-sectional views through embodiments of the sheath.
Figure 25B:
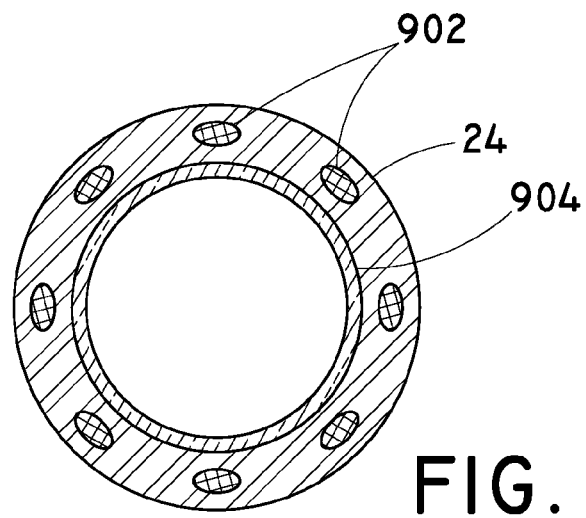
Figure 25C:
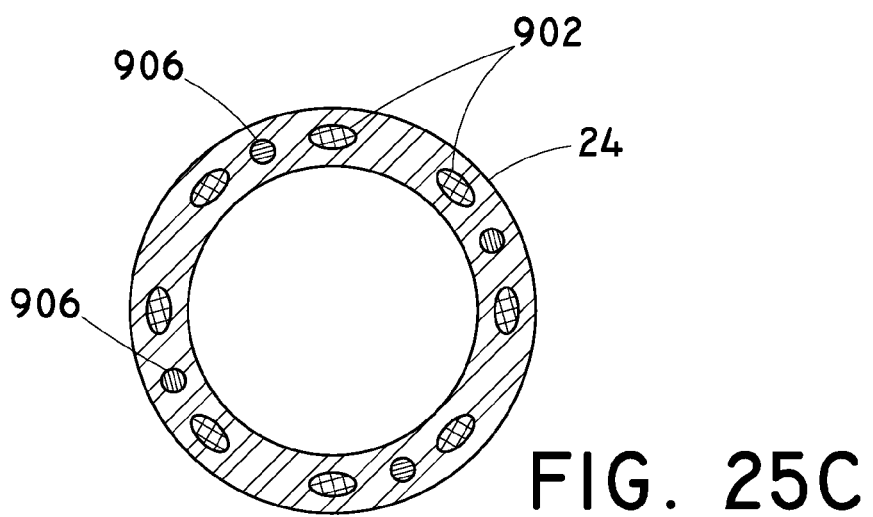

In some embodiments, the outer shaft 24 may optionally include reinforcements to reduce the stretching and compression of the outer shaft 24, for example when the stent 28 is deployed or re-sheathed. Exemplary reinforcements are shown in FIGS. 25A-25C. FIG. 25A illustrates a cross-sectional view through the outer shaft 24 including a plurality of helical braided wires 902 that extend longitudinally along the outer shaft 24. In some embodiments, the braided wires may be formed from nylon. As shown in the cross-sectional view in FIG. 25B, the outer shaft 24 may include the plurality of helical braided wires 902 and may also include a hypo tube 904 extending longitudinally along at least a portion of the outer shaft 24. FIG. 25C illustrates a cross-sectional view of the outer shaft 24 including the plurality of helical braided wires 902 and a plurality of longitudinal wires 906. The wires 906 may be made from any material.

Other suitable biocompatible materials may also be used for any of the components described herein.

Figure 26A:
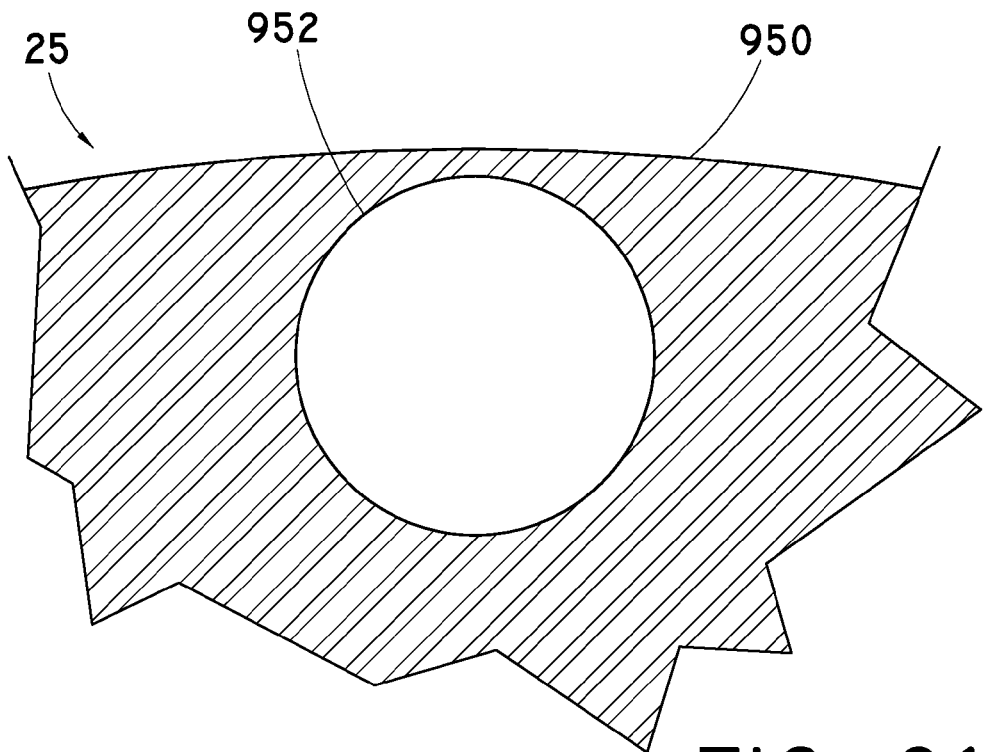
FIGS. 26A-26B illustrate a method of forming a slot in the marker shown in FIG. 5D.
Figure 26B:
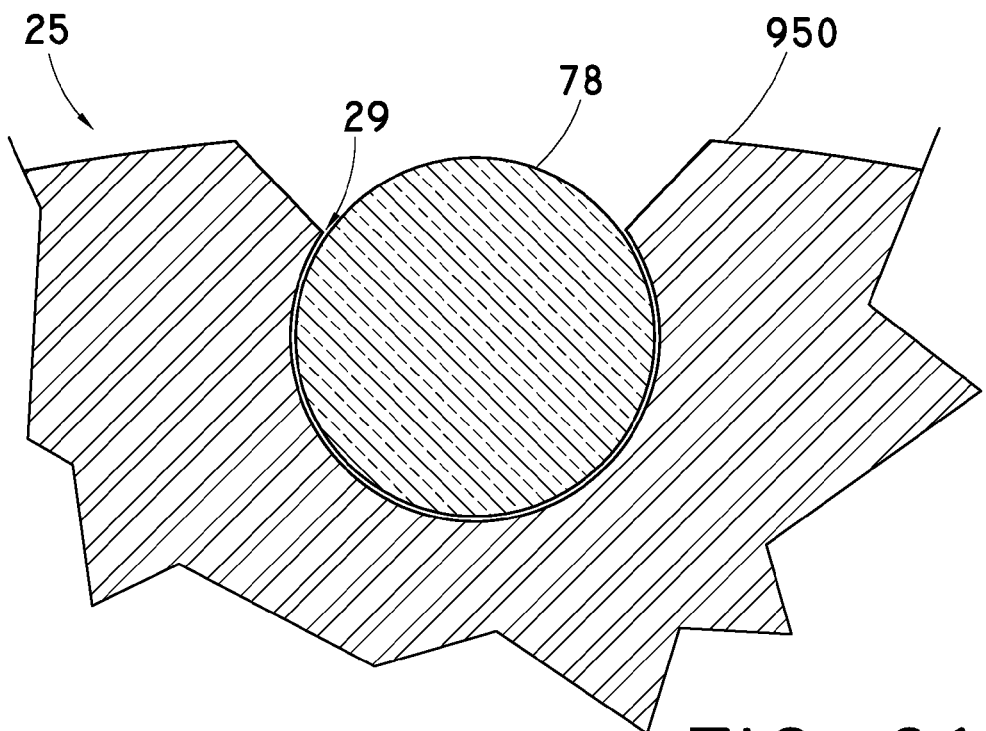

As discussed above with reference to FIG. 5D, slots 29 may be provided in the marker 25 to retain the wires 78 therein. In some embodiments, the slots 29 may be formed by starting with a tube 950 that is extruded with a lumen 952 close to the surface as shown in FIG. 26A. A stylet may be inserted into the lumen 952 so that the stylet deforms the wall of the tube outward. The excess material may be skived off with a blade. As shown in FIG. 26B, the slot 29 is formed with the removal of the excess material and the wire 78 may be positioned within the slot 29.

Operation of the stent delivery systems of the present invention is described with reference to the stent delivery system 10 by way of non-limiting example. Alternative methods of operating the system may also be used. The stent delivery system 10 may be provided in a sterile packaging. The stent 28 may be provided in the expanded configuration 66 or constrained configuration 40 within the packaging. For example, some stent materials may weaken or otherwise deform when stored in a constrained configuration 40 with the longitudinal tension exerting force on the stent during shipping and storage. In some embodiments provided with an outer sheath 32, the outer sheath 32 may be provided to hold the stent 28 in position on the stent region 30 without having the proximal and distal constraining members 44, 46 tensioning the stent. For example, the system 10 may be provided with the handle 26 in the open position 64 and the outer sheath 32 over the stent 28 on the inner shaft 22. Prior to insertion of the distal portion 31 of the system 10 into the patient, the operator may move the handle 26 to the closed position 52 and place longitudinal tension on the stent 28 using the proximal and distal constraining members 44, 46 to constrain the stent 28 against the inner shaft 22. The stent 28 may be provided in the expanded configuration 66 in the absence of a sheath as well and be moved to the constrained configuration 40 by operation of the handle 26 to the closed position 52 prior to delivery to the patient.

Minimal fluoroscopy may be used for placement of the stent 28 within the patient's lumen because of the simultaneous release of the stent. The simultaneous release of the stent 28 means that the midpoint of the stent 28 in the constrained configuration 40 on the inner shaft 22 is the midpoint when the stent 28 is released also so that the stent 28 can be precisely positioned based on the known midpoint of the stent 28. Fluoroscopy is not required during placement of the stent 28 once the placement position has been determined. The stricture length within the patient's lumen at the treatment site is measured using fluoroscopy. Then the stent 28 may be placed at the proper position within the lumen using an endoscope alone.

The outer sheath 32 may include two different sets of distance measurement markings 37, 39, one to be used when the outer sheath 32 is covering the stent 28 and one set to be used when the outer sheath 32 has been withdrawn and locked to the handle 26 (See FIGS. 2 and 3). The markings 37, 39 may be of different colors, for example, to easily identify the two measurements. The operator measures the distance from the incisor teeth to the midpoint of the stricture. The stent delivery system 10 is inserted into the patient using the first set of sheath markings 37 to place the constrained stent 28 in the stricture by measuring the distance relative to the incisor teeth. The sheath 32 is withdrawn proximally and locked to the handle 26 to expose the stent 28. The second set of markings 39 is used once the sheath 32 is withdrawn to measure the distance between the stricture and the incisor teeth to ensure that the stent 28 is still in the correct position relative to the stricture. Because the outer sheath 32 is not used to deploy the stent 28, the markings 37, 39 can be placed clearly on the outside of the sheath and the outer sheath can be locked to the handle 26 and held steady relative to the patient's incisor teeth to increase the accuracy of the stent placement.

The endoscope is positioned within the lumen so the operator can view the proximal side of the stricture. The guidewire 36 is inserted through the stricture and the endoscope is removed. The proper length stent 28 is selected based on the stricture measurement. The operator inserts the distal portion 31 of the stent delivery system into the patient's lumen with the stent 28 in the constrained configuration 40 on the inner shaft 22. The guidewire 36 may be inserted first to navigate a tortuous pathway to the treatment site and the system 10 is delivered over the guidewire 36 to the treatment site. The endoscope may then be placed into the patient's lumen adjacent and parallel to the system 10. Alternatively, the stent delivery system 10 may be inserted into the patient's lumen through the working channel of an endoscope, depending on the size and location of the lumen.

A viewing port of the endoscope is used to identify the proximal end of the stricture at the treatment site. The stent region 30 is positioned within the lumen at the treatment point. For embodiments having a softer inner shaft 22, the stiffening member 67 is inserted through the lumen 69 of the inner shaft 22 to provide support for the longitudinally tensioned stent. The outer sheath 32, if present, is proximally withdrawn and the stent 28 in the constrained configuration 40 is exposed within the patient's lumen. The constrained stent 28 may be moved within the lumen to correctly position the stent 28 at the treatment site. The stent 28 is moved to the expanded configuration 66 by movement of the handle portion 58 to the open position 64 that moves the proximal and distal constraining members 44, 46 to the second position 49 releasing the longitudinal tension on the stent 28. The position of the expanded stent 28 is monitored using the endoscope. The stent 28 may be returned to the constrained configuration 40 by the operator moving the proximal portion 58 of the handle 26 to the closed position 52 and returning the proximal and distal constraining members 44, 46 to the first position 47 to longitudinally tension the stent 28 against the inner shaft 22, for example if the stent 28 is incorrectly positioned. The stent 28 may be moved from the constrained configuration 40 to the expanded configuration 66 as many times as needed.

Once the proper position for the stent 28 is achieved within the patient's lumen, the proximal and distal retaining wires 78, 88 may be proximally withdrawn from the stent 28 to completely release the stent 28 from the proximal and distal constraining members 44, 46. The delivery system 10 is withdrawn proximally from the patient and the endoscope removed.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A stent delivery system comprising:
an elongate shaft including a proximal portion, a distal portion, a lumen extending at least partially therethrough, and a stent receiving portion on the distal portion of the shaft;
a stent positioned at the stent receiving portion of the elongate shaft, the stent having a constrained configuration and an expanded configuration;
a proximal constraining member releasably connected to a proximal portion of the stent and having a first position and a second position;
a distal constraining member, the distal constraining member comprising a distal retaining wire, a first distal loop and a second distal loop, the first distal loop extending through a plurality of peaks of the stent, the distal retaining wire releasably extending through the first and second distal loops, the distal constraining member releasably connected to a distal portion of the stent and having a first position and a second position; the proximal constraining member and the distal constraining member cooperatively apply a longitudinal tensile force to at least a portion of the stent in the constrained configuration with the proximal and distal constraining members each in the first position, the proximal and distal constraining members releasably locking the stent to the elongate shaft and allowing the stent to move between the constrained configuration and the expanded configuration, the stent in the expanded configuration is fully expandable and free from constraint by an outer sheath without release from the elongate shaft.

2. The stent delivery system of claim 1, further comprising a handle operably connected to the proximal and distal constraining members for moving the proximal and distal constraining members between the first position and the second position to move the stent between the constrained configuration and the expanded configuration.

3. The stent delivery system of claim 1, wherein the proximal constraining member comprises a proximal retaining wire to releasably lock the stent to the proximal constraining member.

4. The stent delivery device of claim 3, wherein the proximal constraining member comprises a proximal loop releasably connected to the stent and one retaining wire.

5. The stent delivery system of claim 3, wherein the proximal and distal retaining wires are removable from connection with the stent to completely release the stent from the proximal and distal constraining members.

6. The stent delivery system of claim 1, wherein the stent is repeatedly movable between the constrained configuration and the expanded configuration.

7. The stent delivery system of claim 1, wherein the distal constraining member is connected to the elongate shaft distal to the stent receiving portion.

8. The stent delivery system of claim 7, wherein the proximal constraining member is connected to an outer shaft movably positionable over a portion of the elongate shaft, the proximal constraining member is connected to the outer shaft proximal to the stent receiving portion on the elongate shaft.

9. The stent delivery system of claim 8, wherein the outer shaft and the elongate shaft are movable in equal and opposite directions in relation to each other to move the proximal and distal constraining members in equal and opposite directions in relation to each other to expand and constrain the stent.

10. The stent delivery system of claim 1, further comprising a stiffening member removably positionable in the lumen to support the elongate shaft against the longitudinal force applied to the stent.

11. The stent delivery system of claim 1, further comprising a sheath removably positionable over the stent and a portion of the elongate shaft.

12. A method of implanting a stent in a patient's lumen, the method comprising:
inserting a distal portion of a stent delivery system into the lumen of a patient, the stent delivery system comprising:
an elongate shaft including a proximal portion, a distal portion, a lumen extending at least partially therethrough, and a stent receiving portion on the distal portion of the shaft;

a stent positioned at the stent receiving portion of the elongate shaft, the stent having a constrained configuration and an expanded configuration;

a proximal constraining member releasably connected to the stent and having a first position and a second position;

a distal constraining member, the distal constraining member comprising a distal retaining wire, a first distal loop and a second distal loop, the first distal loop extending through a plurality of peaks of the stent, the distal retaining wire releasably extending through the first and second distal loops, the distal constraining member releasably connected to the stent and having a first position and a second position;

holding the stent in the constrained configuration with longitudinal tensile force applied to the stent by the proximal and distal constraining members each in the first position and cooperatively tensioning the stent for delivery of the stent to the implant site;

positioning the stent at the implant site;

expanding the stent to the expanded configuration by moving the proximal and distal constraining members each to the second position and releasing longitudinal force on the stent, the stent in the expanded configuration is fully expandable and free from constraint by an outer sheath, the proximal and distal constraining members releasably locking the stent to the elongate shaft and allowing the stent to move between the constrained configuration and the expanded configuration without release from the elongate shaft.

13. The method of claim 12, further comprising reapplying longitudinal force to the stent to move the stent from the expanded configuration to the constrained configuration by moving the proximal and distal constraining members to the first position.

14. The method of claim 12, further comprising providing a handle for moving the proximal and distal constraining members in equal and opposite directions between the first position and the second position.

15. The method of claim 12, further comprising providing a removable sheath over the stent and a portion of the elongate shaft and withdrawing the sheath from the stent in the patient's lumen so that the stent is exposed in the constrained configuration.

16. The method of claim 12, further comprising providing a stiffening member extending into the lumen when the delivery device is in the patient's lumen.

17. The method of claim 12, further comprising providing a proximal retaining wire to releasably lock the stent to the stent delivery system using the proximal and distal constraining members and allow the stent to move between the constrained configuration and the expanded configuration without release from the stent delivery system.

18. The method of claim 17, withdrawing the proximal and distal retaining wires to release the stent from the stent delivery system.

19. A system comprising:

an inner elongate shaft including a proximal portion, a distal portion and a lumen extending at least partially therethrough;

an outer elongate shaft including a proximal portion, a distal portion and a lumen extending at least partially therethrough, the inner elongate shaft coaxially extending at least partially within the lumen of the outer elongate shaft, the inner and outer elongate shafts movably positionable relative to each other;

an expandable member having a first end portion and a second end portion and having a constrained configuration and an expanded configuration, the first end portion operably connected to one of the inner and the outer elongate shaft and the second end portion operably connected to the other of the inner and the outer elongate shaft; and a proximal constraining member releasably connected to a proximal portion of the expandable member; and a distal constraining member releasably connected to a position on the expandable member distal to the proximal constraining member, the distal constraining member comprising a distal retaining wire, a first distal loop and a second distal loop, the first distal loop extending through a plurality of peaks of the expandable member, the distal retaining wire releasably extending through the first and second distal loops;

wherein movement of the inner and outer elongate shafts relative to each other in a first direction applies opposing longitudinal force to at least a portion of the expandable member and wherein movement of the inner and outer elongate shafts relative to each other in a second direction releases the longitudinal force on the at least a portion of the expandable member, the proximal and distal constraining members releasably locking the expandable member to one of the inner and the outer elongate shaft and allowing the expandable member to move between the constrained configuration and the expanded configuration, the expandable member in the expanded configuration is fully expandable and free from constraint by an outer sheath without release from one of the inner and the outer elongate shaft.

20. The system of claim 19, wherein the expandable member comprises a stent.

21. The system of claim 20, wherein the proximal and distal constraining members apply opposing longitudinal force to the stent in a first constraining member position to hold at least a portion of the stent in a constrained configuration.

* * * * *